(12) United States Patent
Kotler et al.

(10) Patent No.: US 7,351,527 B2
(45) Date of Patent: Apr. 1, 2008

(54) IMMUNIZING FISH AGAINST VIRAL INFECTION

(75) Inventors: Moshe Kotler, Mevasseret Zion (IL); Arnon Dishon, Jerusalem (IL); Janette Bishara Shieban, Haifa (IL); Maya Ilouze, Jerusalem (IL); Izhak Bejerano, Kibbutz Nir-David (IL); Ayana Benet, Kibbutz Ein-Carmel (IL); Nissim Chen, Givataiim (IL); Marina Hutoran, Jerusalem (IL); Ariel Ronen, Jerusalem (IL)

(73) Assignees: Yissum Research Development Company of the Hebrew University of Jerusalem, Jerusalem (IL); Ministry of Agriculture and Rural Development Dept. of Fisheries and Aquaculture, Beit Dagan (IL)

( * ) Notice: Subject to any disclaimer, the term of this patent is extended or adjusted under 35 U.S.C. 154(b) by 0 days.

(21) Appl. No.: 11/170,793

(22) Filed: Jun. 30, 2005

(65) Prior Publication Data

US 2006/0013828 A1    Jan. 19, 2006

Related U.S. Application Data

(63) Continuation-in-part of application No. PCT/IL03/001097, filed on Dec. 22, 2003.

(30) Foreign Application Priority Data

Jan. 1, 2003    (IL) ..................................... 153775

(51) Int. Cl.
*C12Q 1/70* (2006.01)
*C12N 7/04* (2006.01)
*A61K 39/12* (2006.01)

(52) U.S. Cl. ..................... 435/5; 435/236; 424/204.1
(58) Field of Classification Search ..................... None
See application file for complete search history.

(56) References Cited

U.S. PATENT DOCUMENTS 6,180,614 B1 * 1/2001 Davis ........................ 514/44

OTHER PUBLICATIONS

Hedrick et al,. A Herpesvirus Associated with Mass Mortality of Juvenile and Adult Koi, a Strain of Common Carp, Journal of Aquatic Animal Health, Mar. 2000, vol. 12, No. 1, pp. 44-57.*
Gray et al., Detection of koi herpesvirus DNA in tissues of infected fish, Journal of Fish Diseases, Mar. 2002, vol. 25, No. 3, pp. 171-178.*
Gilad et al., Initial characterization of koi herpesvirus and development of a polymerase chain reaction assay to detect the virus in koi, *Cyprinus carpio* koi, Diseases of Aquatic Organisms, Mar. 2002, vol. 48, pp. 101-108.*

Ronen et al., Efficient vaccine against the virus causing a lethal disease in cultured *Cyprinus carpio*, Vaccine, Dec. 1, 2003, vol. 21, No. 32, pp. 4677-4684.*
Bercovier et al., "Characterization of the koi herpesvirus (KHV) thymidine kinase." Database Entrez Nucleotides, AJ535112, 2002.
Body et al., "Isolation of Virus-Like Particles From Koi (*Cyprinus carpio*) Suffering Gill Necrosis." Bull. Europ. Assoc. Fish Path., 20, 87-88, 2000.
Calle et al., "Herpesvirus-Associated Papillomas in Koi Carp (*Cyprinus carpio*)." J. Zoo and Wild Med., 30, 165-169, 1999.
Dawes J., "Koi Virus Disease Update." Ornamental Fish Intl J., 39, 2002.
Fenner et al., "Chapter 12: Immunization Against Viral Diseases." Medical Virology. New York: Academic Press Inc., 1970.
Gilad et al., "Initial characteristics of koi herpesvirus and development of a polymerase chain reaction assay to detect the virus in koi, *Cyprinus carpio* koi." Dis Aquat Org., 48, 101-108, 2002.
Gilad et al., "Molecular comparison of isolates of an emerging fish pathogen, koi herpesvirus, and the effect of water temperature on mortality of experimentally infected koi." J. Gen. Virology, 84, 2661-2668, 2003.
Gray et al. "Detection of koi herpes virus DNA in tissues of infected fish." J. Fish Dis., 25, 171-178, 2002.
Hedrick et al., "Herpesviruses Detected in Papillomatous Skin Growths of Koi Carp (*Cyprinus carpio*)." J. Wild Dis., 26, 578-581, 1990.
Hedrick et al., "A Herpesvirus Associated with Mass Mortality of Juvenile and Adult Koi, a Strain of Common Carp." J. Aqua Animal Health 12, 44-55, 2000.
Kim et al., "Truncated Particles Produced in Fish Surviving Infectious Hematopoietic Necrosis Virus Infection: Mediators of Persistence?" J. Virol., 73, 843-849, 1999.
Miyazaki et al., "Viremia-associated ana-aki-byo, a new viral disease in color carp *Cyprinus carpio* in Japan." Dis. Of Aqua Organ., 39, 183-192, 2000.
Neukirch et al., "Isolation and preliminary characterization of several viruses from koi (*Cyprinus carpio*) suffering gill necrosis and mortality." Bull. Europ. Assoc. Fish Path., 21, 125-134, 2001.
Oh et al., "A Viral Disease Occurring in Cultured Carp *Cyprinus carpio* in Korea." Fish Path., 36, 147-151, 2001.
Ronen et al., "Efficient vaccine against the virus causing a lethal disease in cultured *Cyprinus carpio*." Vaccine, Butterworth Scientific, 21, 4677-4684, 2003.
Sano et al. "A Herpesvirus Isolated from Carp Papilloma in Japan." Fish and Shell Path., 32, 307-311, 1985.
Sano et al., "*Herpesvirus cyprini*: lethality and oncogenicity." J. Fish Dis., 14, 533-543, 1991.

(Continued)

*Primary Examiner*—Bruce R. Campell
*Assistant Examiner*—Sharon Hurt
(74) *Attorney, Agent, or Firm*—The Nath Law Group; Gray M. Nath; Susanne M. Hopkins

(57) ABSTRACT

The present invention provides the isolated causative agent of the disease affecting *Cyprinus carpino* and a method for its isolation. The invention further provides avirulent forms, e.g., live-attenuated form, inactivated form and genetically modified forms of the virus which may be used for vaccination of susceptible fish.

20 Claims, 10 Drawing Sheets

OTHER PUBLICATIONS

Figure 1:
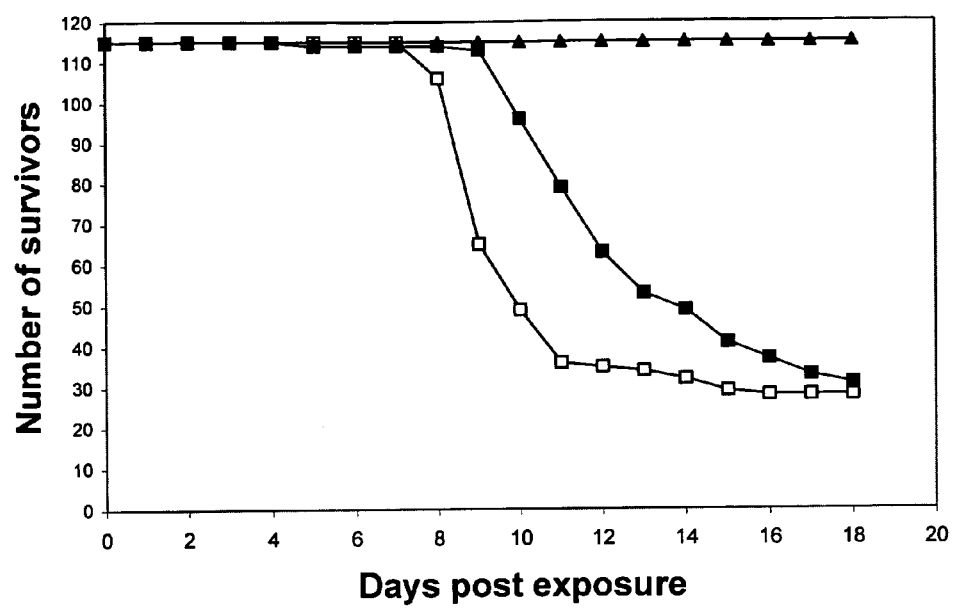

Shchelkunov et al. "Infectivity experiments with *Cyprinus carpio* iridovirus (CCIV), a virus unassociated with carp gill necrosis." J. Fish Dis., 13, 475-484, 1990.

Walster C., "Clinical observations of severe mortalities in koi carp, *Cyprinus carpio*, with gill disease." Fish Vet. J., 3, 54-58, 1999.

De Kinkelin, P. et al., "Eighteen years of vaccination against viral haemorrhagic septicaemia in France", *VET RES.*, vol. 26, Nos. 5-6, pp. 379-387 (1995).

Ilouze, M. et al., "Characterization of a Novel Virus Causing a Lethal Disease in Carp and Koi", *MICROBIOL. MOL. BIOL. REVIEWS*, vol. 70, No. 1, pp. 147-156 & No. 3, pp. 857 (Mar. 2006).

* cited by examiner

⊏▭▭⊐ 89-94% Identity         ▬▬▬ 100% Identity
⊏═⊐ 95-99% Identity          ┈┈┈ Multiple alignment connecting line

IMMUNIZING FISH AGAINST VIRAL INFECTION

This is a Continuation-In-Part of International PCT Application No. PCT/IL2003/001097 filed Dec. 22, 2003, which claims priority from Israeli Patent Application No. 153775 filed Jan. 1, 2003, the contents of which are hereby incorporated by reference in their entirety.

FIELD OF THE INVENTION

This invention relates to the control of viral infection in fish.

REFERENCES

The following references are presented herewith for the better understanding of the invention and should not be construed to the patentability of the invention.

Body A., Lieffring F., Charlier G, Collard A., Bull. Europ. Assoc. Fish Path., 20, 87-88, 2000.
Calle P. P., McNarnara T., Kress Y, J. Zoo and Wild Med., 30, 165-169, 1999.
Dawes J., OFI Journal, 39, 2002.
Gray W. L., Mullis L., LaPatra S. E., Groff J. M., Goodwin A., J. Fish Dis., 25, 171-178, 2002.
Hedrick R. P., Groff J. M., Okihiro M. S., McDowell T. S., J. Wild Dis., 26, 578-581, 1990.
Hedrick R. P., Gilad O., Yun S., Spangenberg J., Marty G, Nordhausen R., Kebus M., Bercovier H., Eldar A., J. Aqua Animal Health 12, 44-55, 2000.
Kim C. H., Dummer D. M., Chiou P. P., Leong J. A., J. Virol., 73, 843-849, 1999.
Miyazaki T., Okarnoto H., Kageyama T., Kobayashi T., Dis. Of Aqua Organ., 39, 183-192, 2000.
Oh M. J., Jung S. J., Choi T. J., Kim H. R., Rajendran K., Kim Y. J., Park M. A., Chun S. K., Fish Path., 36, 147-151, 2001.
Sano T., Fukuda H., Furukawa M., Fish and Shel. Path., 32, 307-311, 1985.
Sano T., Morita N., Shima N., Akimoto M., J. Fish Dis., 14, 533-543, 1991.
Shchelkunov I., Shchelkunov T., J. Fish Dis., 13, 475-484, 1990.
Walster C., Fish Vet. J., 3, 54-58, 1999.

BACKGROUND OF THE INVENTION

It is estimated that fish disease cost twenty to thirty cents for each dollar spent rearing fish in the USA. Although fish pathogens include fungal, protozoan and bacterial agents, it is viral diseases that most concern hatchery owners, as they are largely uncontrollable. In fact, there are no effective antibiotics or other antiviral agents that work effectively against viruses in fish.

Massive mortality of *Cyprinus carpio* species has been observed in food and ornamental trade fish farms in many countries, resulting in severe financial losses. Although the lethal disease is highly contagious and extremely virulent, morbidity and mortality are restricted to Koi and Common carp populations. Several closely related species, including other Cyprinoids such as Goldfish, were found to be completely asymptomatic to the disease, even following long-term cohabitation with diseased fish sharing the same tank.

The intensive farming of Koi, Common carp and other Cyprinoids in ponds or in captivity results in frequent distribution of viral diseases in these populations. Corona-like virus (Miyazaki, 2000), rhabdovirus (Kim, 1999) iridovirus (Shchelkunov, 1990) and herpesviruses (Sano, 1985; Hedrick, 1990, 2000; Calle, 1999) have been suggested as the cause for the severe diseases in Cyprinoids. Herpesvirus was detected in papillomatous skin growth of Koi carp in North America (Hedrick, 1990; Calle, 1999). This carp herpesvirus (CHV) is consistent with herpesvirus cyprini known in Koi carp populations in Japan (Sano, 1985, 1991). A lethal disease observed in Cyprinoids in Israel has also been observed in North America, Europe and Korea (Hedrick, 2000; Walster, 1999; Oh, 2001).

It has been suggested that the disease causing massive mortality of *Cyprinus carpio* species is caused by a Koi herpesvirus (KHV). However, in actuality the KHV virus has only partly been characterized (Hedrick, 2000; Gray, 2002; Body, 2000). Irrespective of the identity of the virus, the disease exhibits a distinct development pattern. Affected fish exhibit sluggish behavior, followed by death. In the period that precedes death, white patches appear on the gills. These are produced by necrotic gill tissue and extensive mucus production and may be accompanied by bleeding (Dawes, 2002).

Currently, there are no methods for controlling the disease except for the destruction of infected stocks and the decontamination of hatchery facilities. Although mortality can reach as high as 100%, some fish can and do survive and at times the survival rate exceeds 20%. These fish then become resistant to subsequent exposures to the virus, remaining healthy despite attempts to reinfect them.

On the basis of these and other related observations, local farmers in Israel established a seven-step protocol designed at creating naturally immune fish that might be considered safe, clean and suitable for sale (Dawes, 2002).

This seven-step protocol involves allowing fish to spawn and hatch in March and grow unsorted until July, at which point they are sorted into different quality categories. The sorted fish are then exposed to the virus for four days through the introduction of sick fish into the tank and are subsequently given two three-month recovery periods. The fish are then allowed to experience the optimal infection window that occurs as the temperatures drop at the beginning of October and are subsequently tested for immunity around January.

SUMMARY OF THE INVENTION

The present invention provides the isolated causative agent of the disease affecting *Cyprinus carpio*. In accordance with the present invention, the agent has been found to be a yet unclassified DNA virus.

It was found that the isolated carp virus DNA (hereon designated as "CV DNA virus") of the invention is a large double stranded DNA virus with the capsid of the virus having a icosahedron morphology, the capsid being of about 90-110 nm in size, as determined by electron microscope. The DNA of the carp virus was found to comprise between about 250,000 and 300,000 base-pairs as determined by pulse field gel electrophoresis and by the analysis of the products obtained from restriction enzyme cleavage. This virus is clearly different from the KHV virus described in the literature.

The carp virus of the invention may have one or more of the following characteristics (found for the specific isolate described below): (a) it is highly contagious, (b) it is capable of being transmitted through water, (c) it induces the disease in a temperature range of 18-25° C. as observed in open air pools and under laboratory conditions, and (d) it has a narrow host range, since even closely related cyprinoid fish were resistant to this virus, which was unable to propagate in epithelioma papillosum cyprini (EPC) cultures.

By one of its aspects, the present invention provides an isolated CV DNA virus that causes viral diseases in fish, in particular fish that are of the species *Cyprinus carpio*.

By one embodiment, the isolated virus of the invention is an enveloped, large double stranded DNA virus with the capsid of the virus having a icosahedron morphology, the capsid being of about 90-110 nm in size, as determined by electron microscopy, the DNA of the virus having between about 250,000 and 300,000 base pairs.

In accordance with another embodiment, the isolated virus of the invention is an enveloped, large double stranded DNA virus with the capsid of the virus having a icosahedron morphology, the capsid being of about 90-110 nm in size, as determined by electron microscopy, the DNA of the virus having between about 260,000 and 285,000 base pairs.

In accordance with yet another embodiment, the isolated virus of the invention is an enveloped, large double stranded DNA virus with the capsid of the virus having a icosahedron morphology, the capsid being of about 90-110 nm in size, as determined by electron microscopy, the DNA of the virus having about 277,000 base pairs.

The CV DNA virus of the invention may be prepared in pure form, namely free of other viruses or microbial material.

The invention also provides, by another of its aspects, a method of isolating said CV DNA virus, which comprises identifying fish suffering from symptoms associated with the CV, harvesting tissues from infected fish, co-cultivation of affected tissue with fish cells until a cytopathic effect ensues in said fish cells, harvesting medium from co-cultivation and isolating the virus particles. Said cells are preferably cultured fin cells. Where the fish are carps, the cells are carp cells, preferably carp fin cells (CFCs). Where the fish are Koi, the cells are Koi fin cells.

The virulent virus may typically be isolated from the tissues of diseased fish, preferably kidney, liver tissues, brain tissues, any part of the nervous system or blood. The virus may also be isolated from any fish secretion or droppings. In the case of carp, the co-cultivation with CFC is typically for a period of 5-6 days, when a cytopathic effect can be observed.

The invention also concerns the virulent CV DNA virus having the depository accession No. CNCM I-3145, deposited with the Collection Nationale de Cultures De Microorganismes (CNCM), Institut Pasteur, Paris, France on Dec. 12, 2003.

One of the uses of the isolated CV DNA virus of the invention is in preparing an avirulent virus form that may be used, in accordance with the invention, for vaccination of fish against infection caused by the CV DNA virus. The avirulent form of the CV DNA virus may for example be an attenuated form of the virus, an inactivated form of the virus, genetically modified form of the virus, naked DNA virus and the like.

Thus, there is provided an avirulent form of the carp DNA virus that causes mortal viral disease in fish, said DNA virus being a large double stranded DNA virus with the capsid of the virus having a icosahedron morphology, the capsid being of about 90-110 nm in size as determined by electron microscopy, the DNA of the virus having between about 250,000 and 300,000 base pairs.

Also provided is an avirulent form of the carp DNA virus that causes mortal viral disease in fish, said DNA virus being a large double stranded DNA virus with the capsid of the virus having a icosahedron morphology, the capsid being of about 90-110 nm in size as determined by electron microscopy, the DNA of the virus having between about 260,000 and 285,000 base pairs.

Furthermore, there is provided an avirulent form of the carp DNA virus that causes mortal viral disease in fish, said DNA virus being a large double stranded DNA virus with the capsid of the virus having a icosahedron morphology, the capsid being of about 90-110 nm in size as determined by electron microscopy, the DNA of the virus having about 277,000 base pairs.

In one specific embodiment of the present invention, the isolated CV DNA virus is used in the preparation of a live-attenuated form of the virus that may be used for vaccination of fish against infection caused by the CV DNA virus.

The present invention also provides a method for the isolation of a live-attenuated virus. In accordance with this method, a virulent form of the virus, that may be isolated as described above, is seeded in a CFC, plaques caused by a virus with a reduced virulence are identified, and the virus is isolated from such a plaque. If desired, the virus may then be purified. Preferably, the isolated viruses are again seeded on a fish cell culture derived from the Common carp or from various other fish species, such as, but not limiting to, Silver carp (*Hypophthalmichthys molitrix*), Gold fish (*Carassius aurata*), and Black carp (*Ctenopharyngodon idella*). The same process may then be repeated a number of times until obtaining substantially attenuated live virus.

The invention also concerns the live-attenuated form of the CV virus having the depository accession No. CNCM I-3146 deposited with the Collection Nationale de Cultures De Microorganismes (CNCM), Institut Pasteur, Paris, France on Dec. 12, 2003.

In another preferred embodiment, the isolated CV DNA virus is used in the preparation of an inactivated form of the virus that may be used for vaccination of fish against infection caused by the CV DNA virus.

A method of inactivating the CV DNA virus discussed hereinbefore is also provided by the present invention. The method comprises isolating the virulent virus, exposing it to a chemical treatment or a physical treatment and thereby obtaining an inactivated CV virus. The chemical and physical treatments may be any such treatment known in the art. The chemical treatment may, for example and without limiting the invention thereto, involve exposure of the virus to organic solvents such as formalin, acetone, methanol, ethanol, etc., in accordance with procedures known in the literature to a person skilled in the art. Physical treatment may involve, for example, UV irradiation or high or low temperatures.

The inactivated virus obtained as discussed in the present application or by any other method known in the art, may not form plaques even at high titer concentrations, or may form plaques only at very high concentrations, as compared to the live-attenuated virus which forms plaques even at minimum concentrations.

In yet another embodiment, the isolated CV DNA virus is used in the preparation of a genetically modified form of the virus that may be used for vaccination of fish against infection caused by the CV DNA virus.

In accordance with another aspect, the present invention provides a live-attenuated form of the CV DNA virus which causes the disease in *Cyprinus carpio* as described hereinbefore. As stated above, the live-attenuated form of said virus may be used for vaccination.

Also provided is an inactivated form of the CV DNA virus which causes the disease in *Cyprinus carpio* as described hereinbefore. This inactivated form of said virus may also be used for vaccination.

By a further aspect, the invention provides a vaccine preparation for immunizing fish against an infection caused by said CV DNA virus, the vaccine preparation comprising, as an active ingredient, an avirulent form of said virus. Such avirulent virus form may be, for example and without limitations, a live-attenuated virus, an inactivated virus, or a combination thereof. The invention also provides, by this aspect, use of the avirulent virus such as a live-attenuated virus, an activated virus or a combination thereof, for the production of said vaccine preparation.

The inactivated virus may be used in as a one-component vaccine or may be used as a poly-component vaccine in combination with the live attenuated virus disclosed hereinbefore or with at least one other vaccine that may be familiar to a person versed in the art. The inactivated virus may be administered simultaneously with said at least one other vaccine or at different times. For example, the inactivated virus may be administered several days prior to the administration of a live-attenuated virus.

In one preferred embodiment, the vaccine preparation comprising an avirulent virus form is in a dry form, e.g. in a powder form, lyophilized, in a compressed pellet or tablet form, etc. In another embodiment, said virus may be in the form of a tissue culture fluid. Said fluid may be stored at the ambience, preferably at −70° C., most preferably as a solution containing glycerol. In one specific example, the tissue culture fluid contains 20% glycerol.

By yet another aspect, the present invention provides a vaccine preparation for passive immunization of fish against an infection caused by said CV virus, the vaccine preparation comprising the serum of immunized fish, said serum obtained from animals, i.e., fish, horses, porcine, bovine, mice, rabbits, etc., immunized with the live-attenuated form of said CV virus. In one preferred case, said animals are fish.

The invention, with respect to this aspect, further provides a method for treating fish against the infection caused by said CV DNA virus. The method comprises the steps of immunizing an animal with the avirulent CV virus of the present invention, collecting the serum of the immunized animal and treating the fish with said serum, thereby achieving immunization of the fish.

The various virus forms disclosed in the present invention may be converted into a dry form by a number of methods. A particularly preferred form of drying is through lyophilization. Prior to drying, e.g. lyophilization procedure, a variety of ingredients may be added to the medium such as preservatives, anti-oxidants or reducing agents, a variety of excipients, etc. Such excipients may also be added to the dry, e.g. lyophilized active-attenuated virus also after the drying step.

Immunization is typically performed by adding the avirulent virus form such as the live-attenuated virus, or the inactivated virus, or a combination thereof to the water containing the fish to be immunized. It is also possible to inject the vaccine preparation directly into the fish. In order to boost the immune response, the preparation may also include a variety of adjuvants, cytokines or other immunostimulants, particularly in the case of preparations that are intended for injection. The vaccine preparation, particularly where it is introduced into the water containing the fish, may also include a variety of stabilizers, antibiotics, etc.

In another aspect of the present invention, there is provided an antibody that binds selectively to the CV virus of the present invention or to a component thereof. In one embodiment, the antibody binds specifically to fish DNA virus or to a component thereof.

By another one of its aspects, the present invention relates to a method for the diagnosis of the disease associated with the CV virus which is described hereinabove, said method comprising isolating tissue from suspected fish and determining the presence of viral markers associated with the CV DNA virus, the presence of which will indicate that the tested fish is infected by the virus.

The invention further relates to a kit comprising an avirulent form of the CV DNA virus, such as a live-attenuated virus of the present invention, for the treatment of the carp virus in fish and instructions on how to use it.

The invention further relates to a diagnostic kit comprising at least one antibody or at least one conjugated antibody for the diagnosis of the disease associated with the CV virus and instructions how to use it. The kit may further contain at least one control antigen or a control tissue sample containing said control antigen.

The diagnostic kit of the present application may be used for diagnosing live or dead fish for the presence of the virus of the invention.

ABBREVIATIONS

CFC—Carp fin cell; CHV—Carp herpesvirus; CNGV—Carp nephritis and gill necrosis virus; CPE—cytopathic effect; CV—Carp virus; EPC—Epithelioma papillosum cyprini; HSV—herpes simplex virus; KHV—Koi herpesvirus; KFC—Koi fin cells; PBS—Phosphate buffered saline; PFU—Plaque forming units; PTA—phosphotungstate; SDS—Sodium dodecyl sulfate; TCI—Total DNA extracted from infected CFC; TCU—Total DNA extracted from uninfected CFC.

BRIEF DESCRIPTION OF THE DRAWINGS

In order to understand the invention and to see how it may be carried out in practice, a preferred embodiment will now be described, by way of non-limiting examples only, with reference to the accompanying drawings, in which:

FIG. 1 shows the kinetics of mortality in Koi carp following co-habitation challenge. Adult fish were divided into three groups of 114, 114 and 115 fish. Group 1 (□) and group 2 (■) were exposed to a contaminated specimen and group 3 (▲) was used as uninfected control. Number of survivors was monitored daily.

FIG. 2 shows electron micrographs of CV harvested from the infected carp fin cells (CFC). Purified virus was negatively stained with 2% of phosphotungstate (PTA). Particle size was in the 96-105 nm range, with an average of 103 nm.

FIG. 3 depicts analysis of CV DNA by agarose gel electrophoresis. In FIG. 3A viral DNA genome was obtained from purified viruses by phenol extraction. Each lane depicts a different protocol: incubation with proteinase K and SDS (lane 2), incubation with SDS alone (lane 3), treatment with pronase and SDS (lane 4) and without pretreatment (lane 5). Linear adenovirus plasmid (pAdEasy-1) DNA cleaved with Cla I (lane 6) and non-cleaved (lane 7) were used as markers. Analysis was performed in 0.8% agarose gel where λ phage marker DNA was loaded in lane 1 and 8. In FIG. 3B, the analysis of CV DNA by pulsed field gel electrophoresis (PFGE) is shown. The same DNA preparations described in FIG. 3A were loaded in lanes 2-7, and additional sample of CV DNA purified by proteinase K was loaded in lane 8. The molecular weight markers used were Hind III cleaved λ phage DNA (lane 9) and ladders (successively larger concatamer of λ DNA 50 to 1000 kb) of ligated λ phage DNA (lane 1). FIG. 3C depicts the results obtained from digestion of CV DNA by restriction enzymes. Viral DNA was incubated with Swa I restriction enzyme in a reaction buffer (100 mM NaCl, 50 mM Tris-HCl, 10 mM $MgCl_2$, 1 mM dithiothreitol, supplemented with 100 µg/ml BSA) at 25° C. for 3 hours. Using PFGE via Contour-clamped Homogeneous Electric Field (CHEF) gels, the reaction products were resolved on a 1% agarose gel, under the following conditions: 6 V/cm, 14° C., for 14 hours. Switch times ramped from 5-35 seconds. Lane 1—uncut viral DNA; Lane 2—viral DNA digested with Swa I restriction enzyme.

Figure 4:
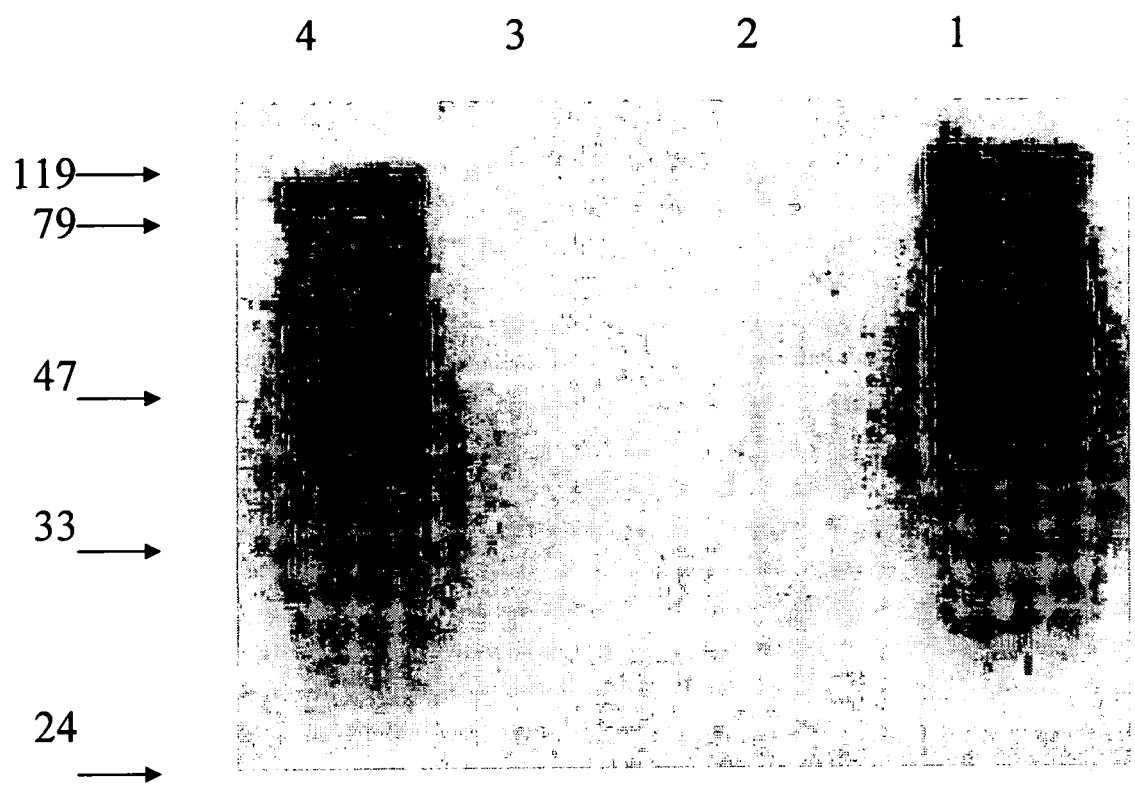

FIG. 4 shows the analysis of CV viral protein. Adenovirus, HSV-1 and carp virus were purified from tissue culture medium by sucrose gradients. The viral pellets were boiled in Laemeli buffer and separated by electrophoresis on two parallel 10% acrylamid gels. One gel was stained with Coomassie blue and is shown in panel A. The other gel was transferred to PVDF membrane and stained with rabbit anti carp virus, as shown in panel B. The serum reacts with CV proteins (right lane) but not with the herpes or adenovirus proteins.

Figure 5A:
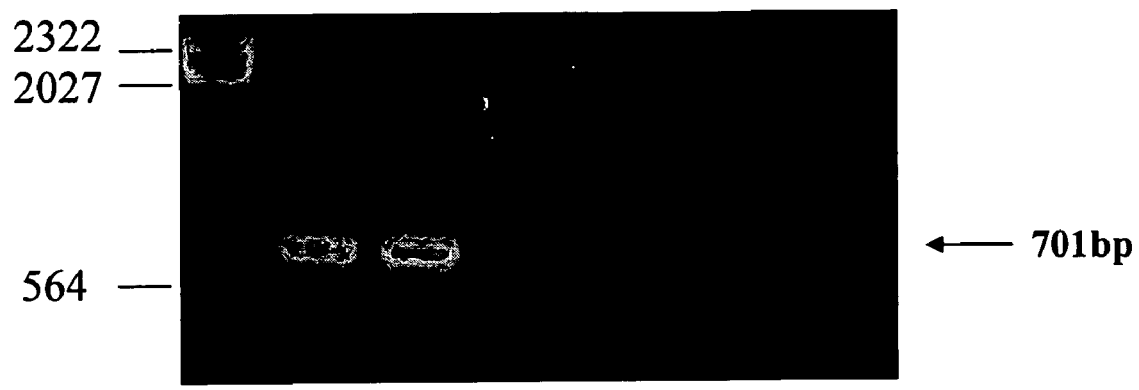
Figure 5B:
Figure 6A:
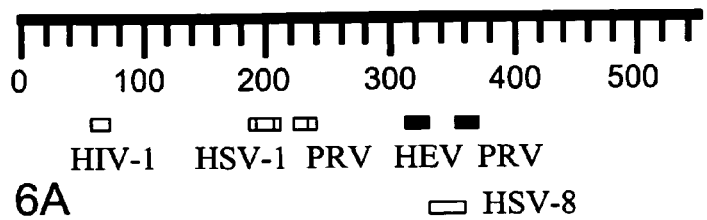
Figure 6B:
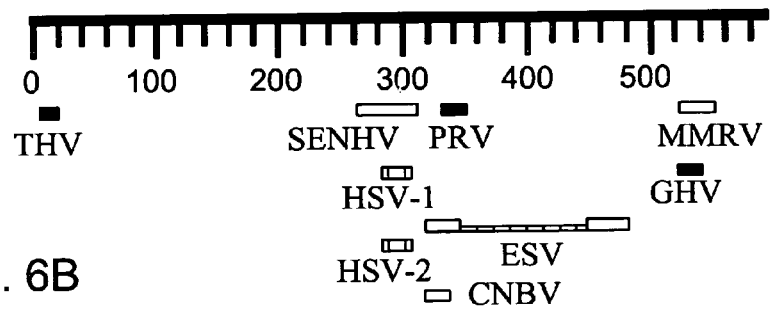
Figure 6C:
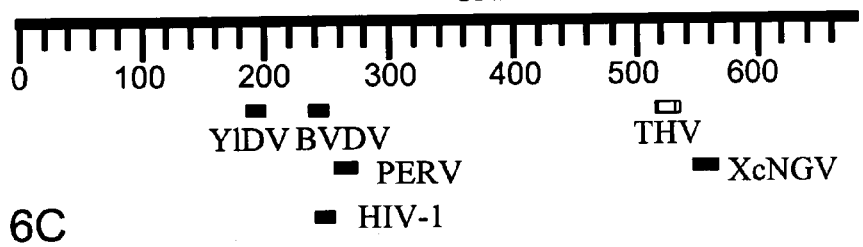
Figure 6D:
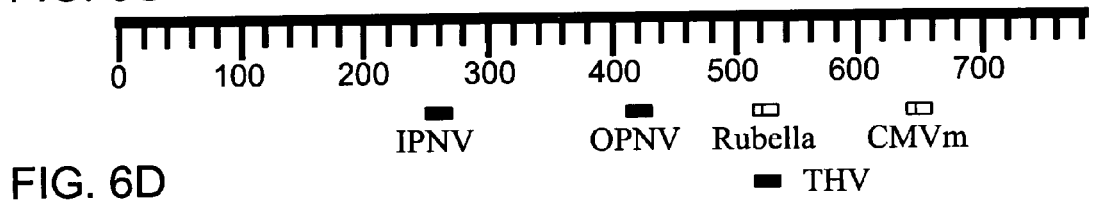
Figure 6E:
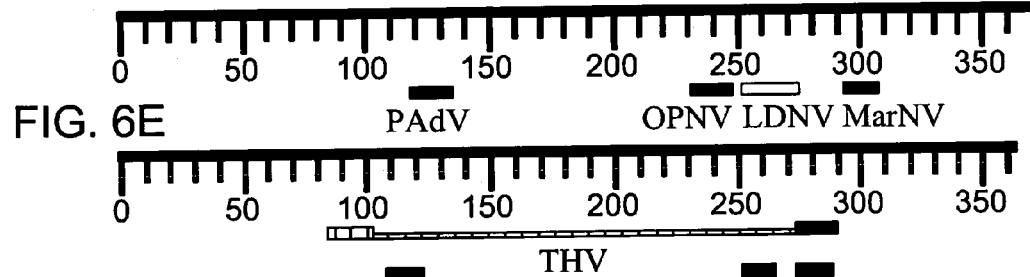
Figure 6F:
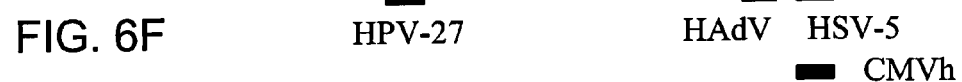

FIG. 5 depicts identification of CV genome fragments amplified by PCR from CFC DNA and from fish organs. Total DNA extracted from infected (TCI), uninfected (TCU) CFC, viral DNA (CV) and DNA from liver of sick and naïve fish (LI and LU, respectively) and from sick and naïve kidney (KI and KU, respectively). M=molecular weight DNA marker. Primers used for DNA amplification were derived from clone D. AP1-AP2 and AP1-AP3 primers were used in the PCR (panel A and panel B, respectively).

FIGS. 6A-F depict homology of sequences in CV genome and other viral sequences. The viral DNA clones were sequenced and analyzed by using the BLAST program of PubMed (NIH). The abbreviation used in this figure are as follows: Herpes simplex virus 1, 2, 5 and 8 (HSV-1, HSV-2, HSV-5 and HSV-8 respectively); Pseudorabies virus (PRV); Gallid herpesvirus (GHV); Macaca mulata rhadinovirus (MMRV); Tupaia herpesvirus (THV); Mouse cytomegalovirus (CMVm); Human cytomegalovirus (CMVh); Marmoset herpesvirus (MarHV). All the above-mentioned viruses belong to the Herpesviridae. Spodoptera exigua nucleopolyhedrovirus (SENHV), Xestia c-nigrum granulovirus (Xc-NGV), Lymatria dispar nucleopolyhedrovirus (LDNV); Orgyia pseudosugata nucleopolyhedrovirus (OPNV) and Culex nigripapus baculovirus (CNBV) are members of the Baculoviridae; Ectocarpus siliculosus virus (ESV) is an Algal virus. Yaba-like disease virus (YlDV) is a Poxvirus. Human immunodeficiency virus type-1 (HIV-1), Human endogenous virus (HEV) and Porcine endogenous retrovirus (PERV) are members of the Retroviridea. Porcine adenovirus (PAdV) and Human adenovirus (HAdV) are members of the adenovirus group. Bovine viral diarrhea virus (BVDV) is a flavivirus. Infectious pancreatic necrosis virus (IPNV) is bimavirus. Rubella virus (Rubella) is a togavirus. Human papillomavirus type 27 (HPV-27).

Figure 7A:
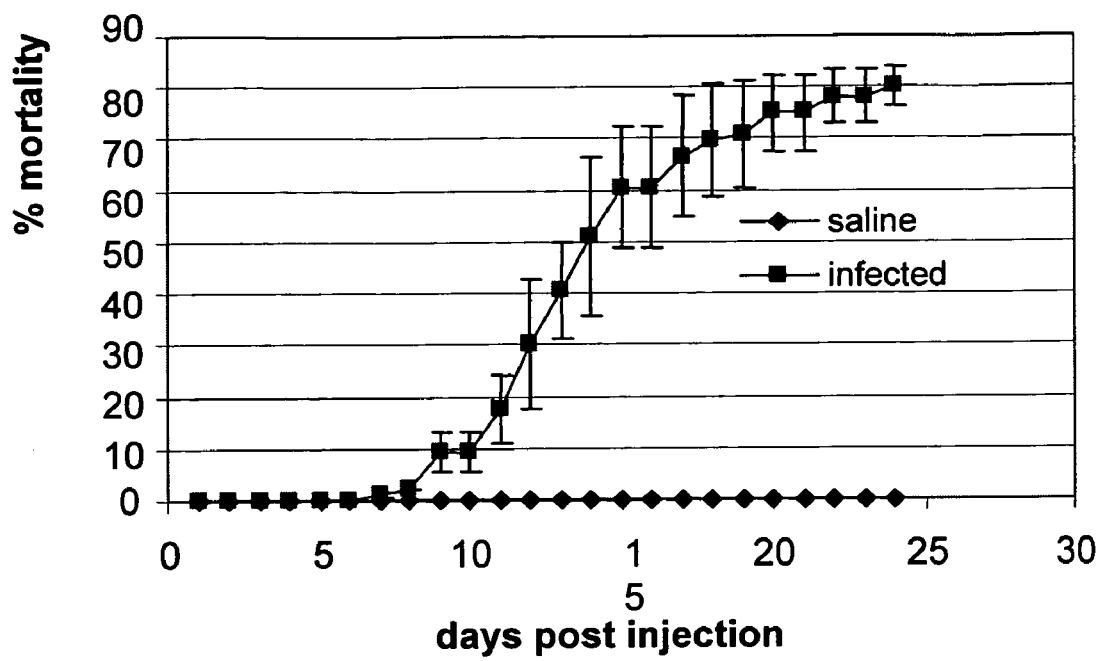
Figure 7B:
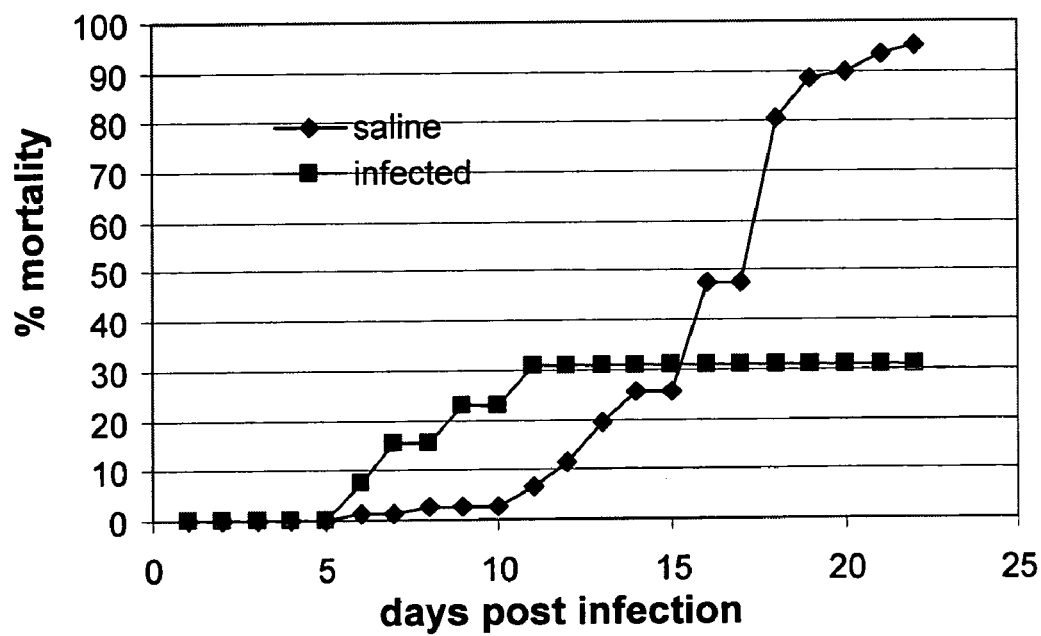

FIGS. 7A-B show the results of infection of fish with the virulent virus. FIG. 7A shows cumulative mortality in a group of 50 naive fish infected with the virulent virus. FIG. 7B depicts the mortality of the fish which survived the initial infection and which were challenged by cohabitation with diseased fish.

Figure 8A:
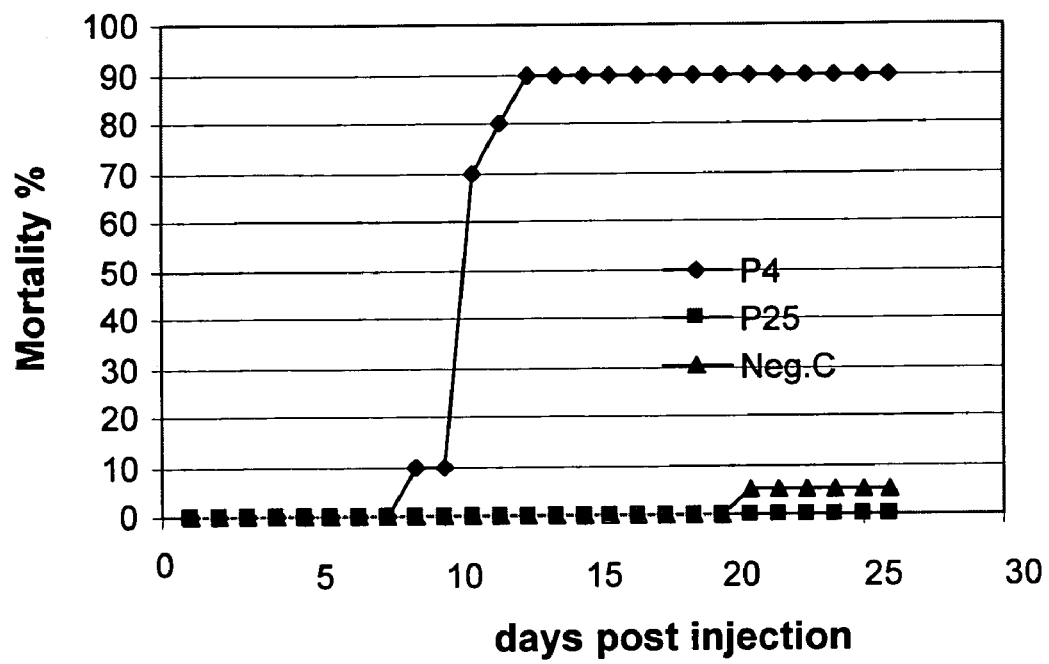
Figure 8B:
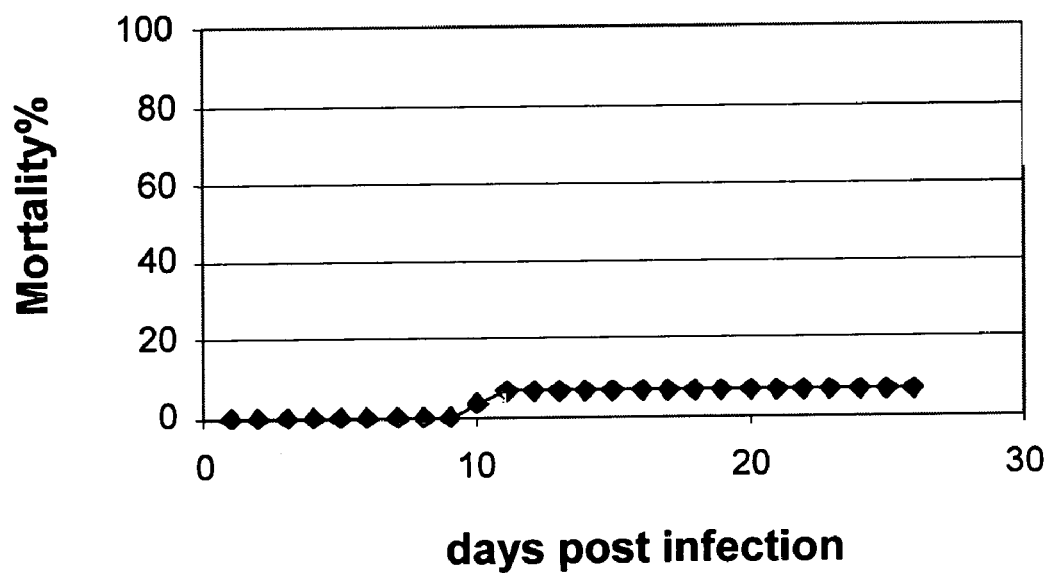

FIGS. 8A-B show results obtained from the infection of fish with live attenuated virus. FIG. 8A depicts mortality of fish post injection (I.P) with the live-attenuated virus at a concentration of $6×10^3$ PFU/ml. FIG. 8B shows mortality of fish which survived initial exposure to the attenuated virus and were challenged with sick fish.

Figure 9:
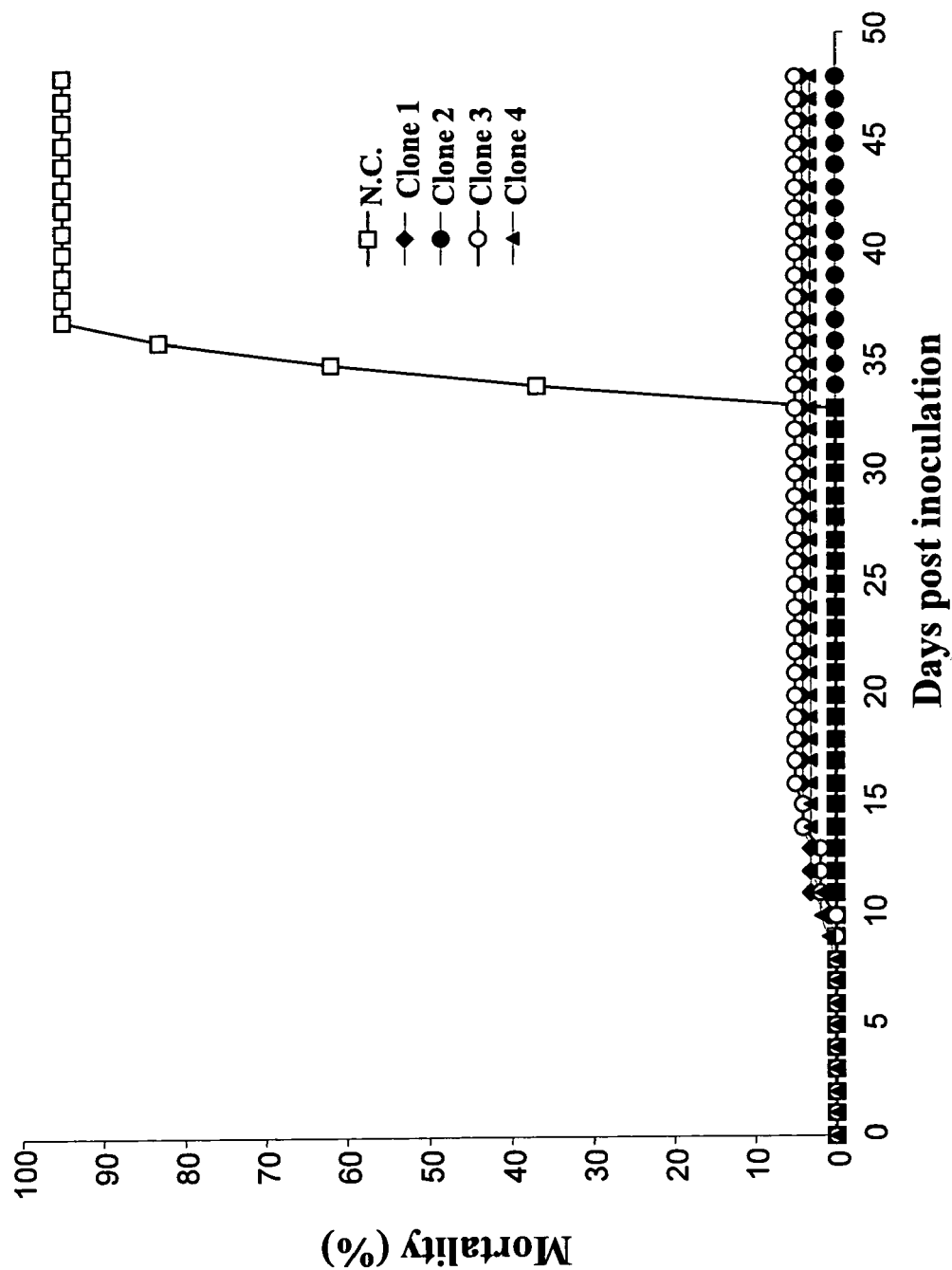

FIG. 9 depicts the mortality rate in vaccinated fish following a challenge infection. Fish (n=100 fish in each group, average weight of 50 g) were vaccinated by I.P injection of 4 cloned viruses derived from the CV virus from transfer P26. Fish injected with PBS were used as negative control, (N.C). Twenty five days post infection, five fish were re-challenged by cohabitation with sick fish.

Figure 10:
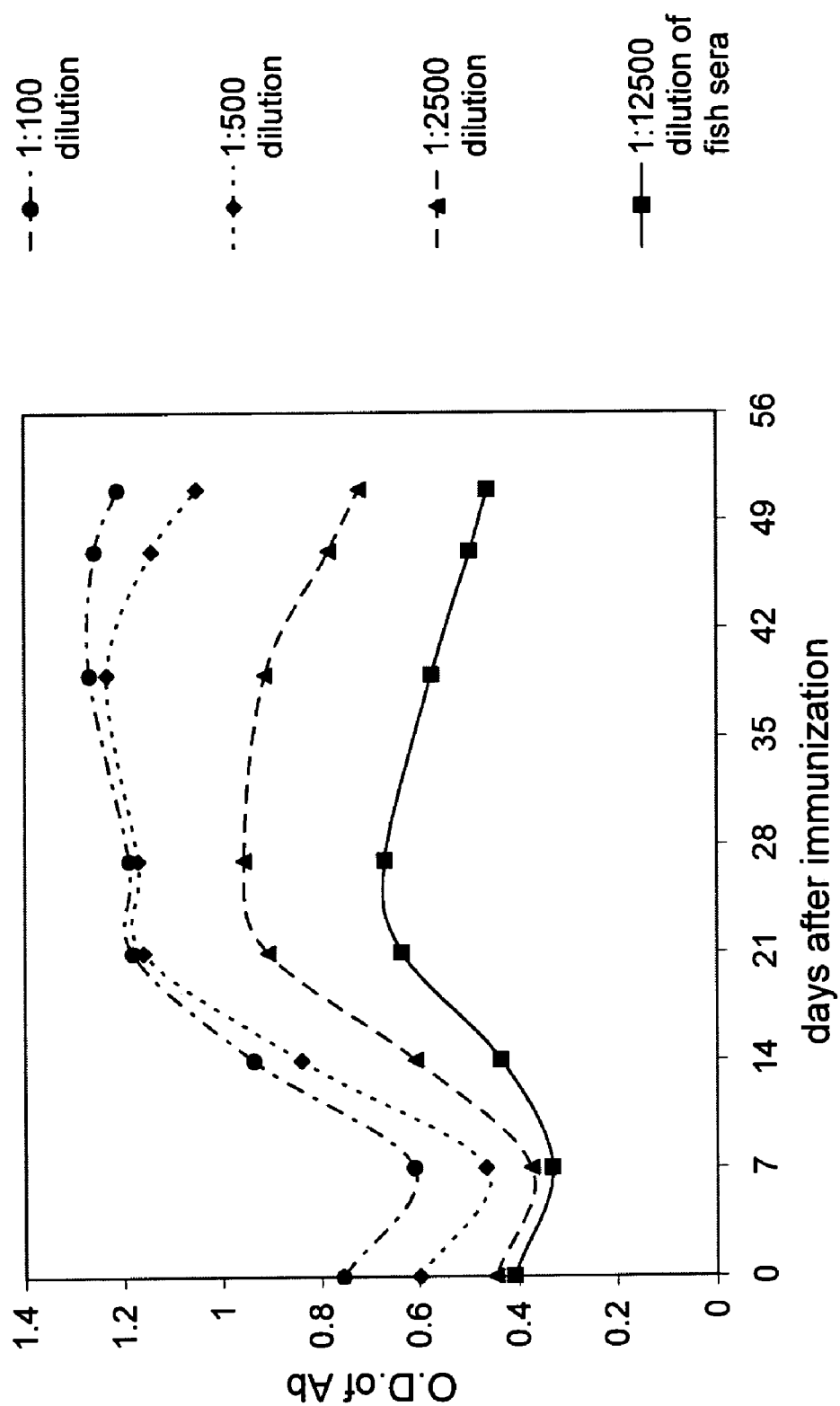

FIG. 10 depicts the kinetics of anti-CV antibody formation in carps immunized against the attenuated virus.

DETAILED DESCRIPTION OF THE INVENTION

In the following, the invention will be illustrated in reference to some non-limiting specific embodiments.

The terms "carp DNA virus" (CV DNA or CV virus) or "carp nephritis and gill necrosis virus" (CNGV), as used hereinbefore and hereinafter are used alternative and synonym expressions used to denote the novel virus of the invention having the characteristics outlined above and below. It should be understood that these terms, namely, CV or CNGV, do not limit the invention to any particular isolate of said virus. Any virus that has the novel characteristics described herein is encompassed by the invention.

The term "virus", in the context of the present application refers, without limitations, to closely related strains of the specific isolate described below, namely any strain, which shares similar genotype and/or phenotype characteristics with this isolated strain. This includes slightly modified forms or variants of the virus, which retain the same functional activities, namely, additions, deletions or alternations of amino acid or nucleotide.

The term "avirulent virus form", in the context of the present invention refers, without limitations, to a virus which is absent of all disease-producing abilities. Such avirulent viruses may be attenuated viruses, inactivated virus and the like which are used in all types of immunizations including active and passive immunizations. Also encompassed within the scope of the invention, any natural avirulent counterpart whose ability to cause the disease described herein is diminished.

The term "fish" refers to any aquaculture fish affected by CV virus, included are food and ornamental trade fish, at any stage of their development, e.g. larvae, fry or adult fish. Also included under this term are any other aquaculture living that may be affected by the CV virus, or that may be an infectious animal that does not itself express or display any of the characteristic behavior of diseased carp infected by the CV virus.

FIG. 1 depicts the exposure of captive naive carp to infected specimens taken from a contaminated hatchery. The exposure of fish to the contaminated specimen resulted in high mortality. On average 74% (87 and 84 fish, respectively) of the fish died 8-13 days post exposure. However, all fish in the control group survived during the 21-day period of the experiments.

Three to four days before death, fish ceased eating, and displayed abnormal behavior, such as fatigue and gasping movements in shallow water. In addition, fish exhibited uncoordinated movements and erratic swimming, characteristic of neurological disorders. Neurological signs, such as decline in frequency of tail movements and loss of equilibrium, were observed in several fish. Similar symptoms were previously described in Koi and Common carp in USA (Hedrick, 2000). These signs were followed by the appearance of severe necrosis of gill tissue, superficial hemorrhages and increased mucous secretion on the skin. Necropsy of sick fish revealed petechial hemorrhages in the liver and other non-consistent pathological changes, suggested symptoms of a secondary infection (not shown).

In similar experiments conducted in tanks, where fish were hatched at a temperature of 29° C., all the exposed fish survived during the 22-day period (data not shown). These results clearly show that the virus causing the disease is easily transmitted through water and is highly contagious. The virus produces a high rate of mortality, but the occurrence of the disease is restricted to a water temperature of 18-25° C.

In accordance with the present invention, a method is provided for isolating the CV virus characterized hereinbefore, said method comprises identification of fish suffering from symptoms associated with the CV virus, co-cultivation of affected tissues with carp fin cells until a cytophatic effect ensues, harvesting medium from co-cultivation of CFC with affected tissues and isolating the virus particles.

In one specific example, the virus was isolated from infected specimens according to the following procedure. Co-cultivation of cells taken from kidney (11 specimens) and liver (5 specimens) of infected fish with CFC resulted in the appearance of cytopathic effects (CPE) 5-6 days post inoculation, while co-cultivation of brain blood cells or sera taken from diseased carp did not result in CPE. Ten days post co-cultivation cultured cells lost their attachment to the flask bottom and died. Medium harvested from CFC co-cultivated with kidney, liver or brain cells (5-7 days post infection) was first clarified of cells and cell debris by centrifugation and then used to titer the virus in fresh CFC flasks.

Figure 2:
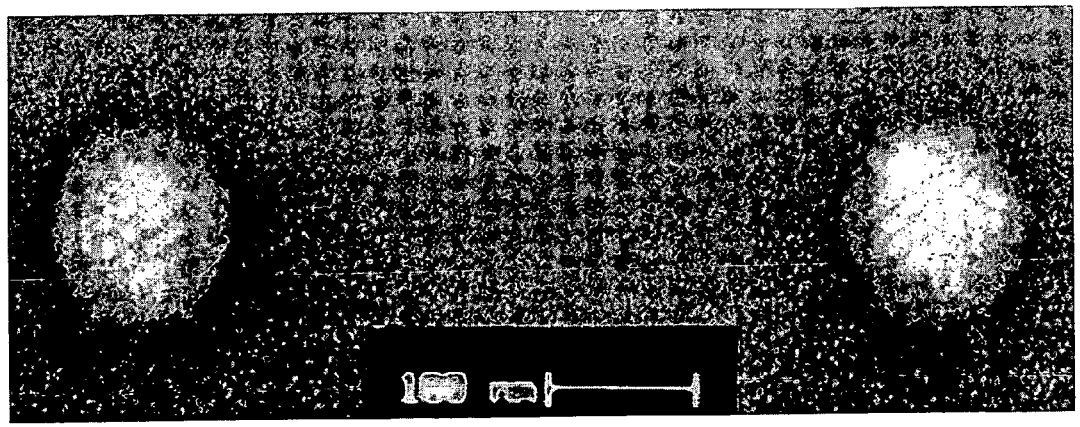

Medium harvested from infected CFC cultures was clarified by centriftigation and purified on sucrose gradients. A clear band at 37-39% sucrose was removed from the gradients, diluted tenfold in PBS and pelleted by centrifugation. The pellets were suspended in 500 µl of PBS and samples were taken for titration on CFC and for electron microscopy analysis. The titer of the purified virus preparation in the medium was $10^6$-$10^7$ PFU/ml. FIG. 2 shows a pair of viral particles of this preparation, completely free of cell debris. The particles are negatively stained and show their symmetric icosahedral morphology with an average core diameter of 103 nm, resembling the core of herpesviruses (Riozman et al., Exp. Med. Biol., Vol. 278, 285-291, 1990).

Table 1A shows that naive fish inoculated with clarified culture media from uninfected CFC remained asymptomatic. However, 75% and 82% of the fish inoculated with infected cell extracts, or with clarified media harvested from infected cultures, respectfully, died within 15 days post intraperitoneal injection. These fish developed the typical pathologic signs identical to those observed in the infected fish grown in the ponds.

Kidney cells taken from inoculated specimens exhibiting the disease symptoms were co-cultivated with CFC. The titer of the virus harvested from the co-cultivated cultures was $1.5 \times 10^2$-$1.8 \times 10^2$ PFU/ml on CFC as determined by the plaque assay, as shown in Table 1B. Medium harvested from these infected CFC was used to re-infect naive juvenile fish. Four out of 10 fish died from the disease, 9 to 14 days post infection (Table 1C).

This 'ping-pong' type of experiment, which was serially repeated three times, clearly attests to the fact that the virus isolated from infected fish and propagated in CFC is indeed the etiologic agent of the disease.

TABLE 1A

Isolation of the virus responsible for the mortality in carp.

| Fish: | Inoculation with: | | |
|---|---|---|---|
| | infected cell extracts: n = 20 | media from uninfected CFC: n = 15 | media from infected CFC: n = 17 |
| dead fish | 15 (75%) | 0 (0%) | 14 (82%) |

TABLE 1B

CFC co-cultivation
Fish inoculated with:

| infected cell extracts | uninfected CFC medium | media from infected CFC |
|---|---|---|
| $1.8 \times 10^2$ plaques | 0 plaques | $1.5 \times 10^2$ plaques |

TABLE 1C

Reinfection of juvenile carp

| Fish: | Inoculation with: | | |
|---|---|---|---|
| | infected cell extracts | media from CFC | media from infected CFC |
| dead fish | — | 0 (0%) | 4 (40%) |

Figure 3A:
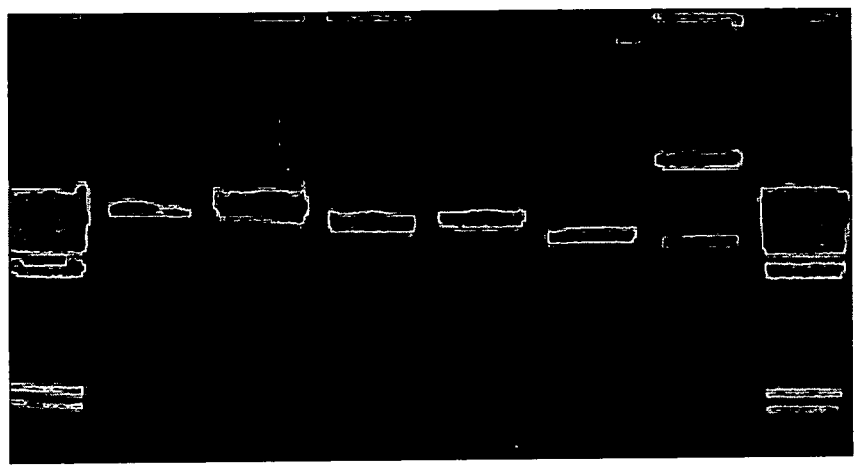

FIG. 3A shows a comparison of the viral DNA genome as obtained from purified viruses by phenol extraction, following these various protocols: incubation with proteinase K and SDS (FIG. 3A, lane 2), incubation with SDS alone (lane 3), treatment with pronase and SDS (lane 4) and without pretreatment (lane 5). The DNA preparations were analyzed by agarose gel electrophoresis (0.8%). The genomic CV DNA migrates in the agarose gel as 25-35 Kb DNA according to the λ phage marker DNA. The linear adenovirus plasmid (pAdEasy-1) DNA cleaved with Cla I (lane 6), used as a marker, migrated to about the same distance.

Figure 3B:
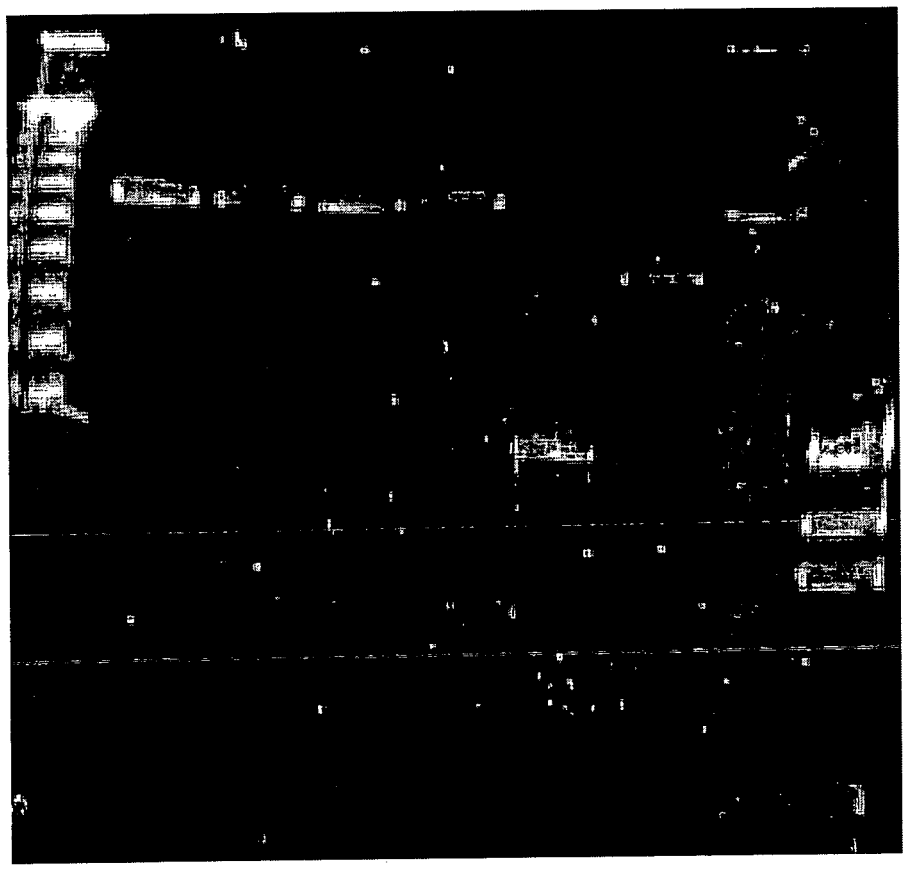
Figure 3C:
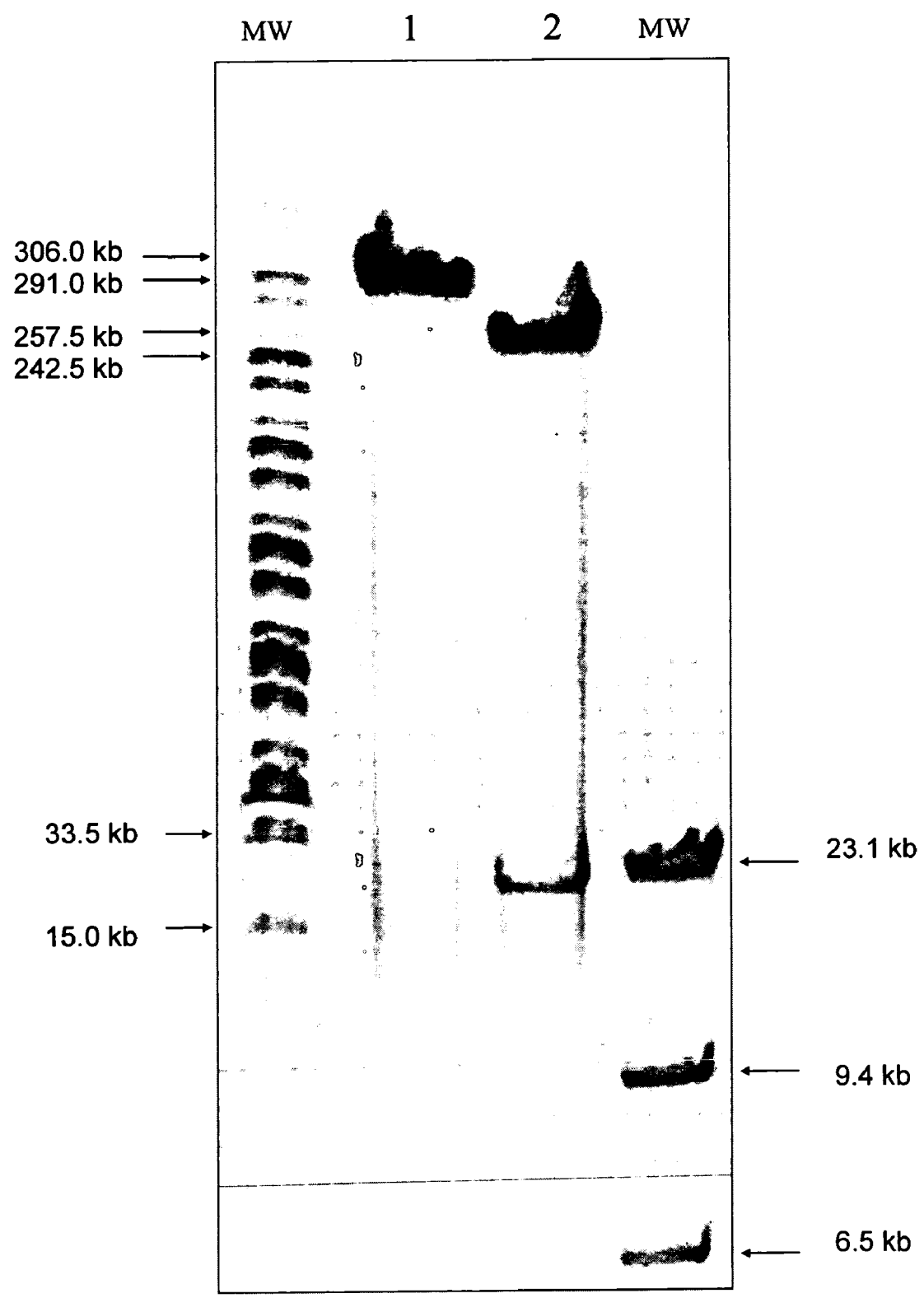

In order to determine the weight of the CV genomic DNA, the same DNA preparation described in FIG. 3A were analyzed by Pulsed Field Gel Electrophoresis (PFGE), as shown in FIG. 3B. All four CV DNA preparations migrated very slowly in the gel to the 250-300 Kb marker of a λDNA marker. The pAdEasy-1 circular, but not the linear plasmid DNA also migrated slowly in the gel as a 150-200 Kb λDNA marker.

An additional support that the CV is a large DNA virus of about 275 kb was obtained by restriction enzyme digestion of the CV DNA and is depicted in FIG. 3C. Lane 1 of FIG. 3C shows the size of the uncut CV DNA being about 275 kb. The cleavage with Swa I resulted in two bands of 20 and 255 kb (Lane 2).

Analysis of the CV viral protein using Coomassie blue staining showed that the CV was distinctly different from the adenovirus and the HSV-1 viruses. Additionally, as is shown in FIG. 4, staining with rabbit anti carp virus antibodies, revealed that the serum reacts with CV proteins only and not with the herpes or adenovirus proteins.

Thus, in another aspect of the present invention, there is provided an isolated antibody that binds selectively to the CV virus of the present invention or to a component thereof. In one embodiment, the antibody is in immobilized form.

The BamHI- EcoRI viral DNA fragments were cloned into Bluescript plasmids (Alting-Mees et al., Nucl. Acids Res., Vol. 17, 9494, 1989), and viral DNA clones were sequenced and analyzed by the BLAST Program (Altchul et al., Nucl. Acids Res., Vol. 25, 3389-3402, 1997 and Short et al., Nucl. Acids Res., Vol. 16, 7583-7600, 1988). By using internal primers derived from sequences of clones A-D, it was proven that the clones represent viral DNA. FIG. 5 shows that the primers derived from clone D, for example, are efficient in amplifying appropriate fragments from viral DNA, from DNA of infected cultured cells and from sick fish, but not from uninfected CFC and naive fish. Similar results were also obtained from clones A-C (results not shown). Analysis of more than 3,500 bp derived from the CV genome did not reveal fragments longer than 45 bp homologous to viral genomes described in the GeneBank (FIG. 6). Although the CV clones bear only small fragments homologous to other viruses, many of these stretches are derived from members of the Herpesviridae and Baculoviradae families.

By one of its aspects, the present invention relates to a method for diagnosing the disease associated with the CV virus, said method comprising isolating tissue from suspected fish and determining the presence of viral markers associated with the CV DNA virus, the presence of which will indicate that the tested fish is infected by the virus of the present invention.

The term "tissue" relates to any tissue obtained from a specific organ, tissues obtained from several organs, a whole fish, or blood. Further included under this term, any organ, or parts thereof used for the diagnosis of the disease. Preferably the tissues are tissues harvested from the gills, kidneys, spleen, liver, brain, any part of the nervous system or intestine. The term also encompasses any fish secretion or droppings.

In accordance with said diagnostic method, the disease may be diagnosed by, without limiting the methods thereto, PCR, as described hereinbefore, by immunohistochemistry as described hereinafter, and/or by testing the antiviral fish sera by ELISA, as described hereinafter.

Methods such as AP (alkaline phosphatase), HRP (Horse reddish peroxidase) and FITC (fluorescein isothiocynate-conjugate) are also utilized in the various diagnostic protocols (see experimental section for Examples).

In accordance with another aspect, the present invention provides a live-attenuated form of said CV DNA virus. The term "live-attenuated" or "attenuation" refers to virus forms which lost their virulence or to the process by which the viruses lose their disease-producing abilities. Various approaches are known for the development of live-attenuated viruses. Attenuation may be achieved by limiting infection to an area of the body in which disease does not develop (Virology, $2^{nd}$ ed., Raven Press, NY, 1990) or by serial passage of the virus in cell cultures prepared from an un-natural host, during which passage the virus sustains mutations.

There are several advantages in utilizing attenuated live virus vaccines such as that of the present invention. In general, live virus vaccines activate all phases of the immune system, resulting in a balanced response, systemic and local, immunoglobulin and cell mediated. Live virus vaccines also stimulate an immune response to each of the protective antigens of the virus, obviating the difficulties that arise from selective destruction of one of the protective antigens that may occur during preparation of an inactivated vaccine. In addition, immunity induced by live virus vaccines is generally more durable, more effective and more cross-reactive than that induced by inactivated vaccine, and is also less costly and more easily administered (Virology, $2^{nd}$ ed., Raven Press, NY, 1990).

By a further aspect, the present invention provides a method for the isolation of said live-attenuated virus comprising seeding of a virulent virus in fish cell culture, preferably obtained from the caudal or dorsal fins of the Koi or common carp, identifying plaques caused by a virus with a reduced virulence and isolating the progeny virus from such a plaque.

The isolated virus may be again seeded on a fish cell culture derived from the common carp or from various other fish species, such as, but not limiting to, Silver carp (*Hypophthalmichthys molitrix*), Gold fish (*Carassius aurata*), and Black carp (*Ctenopharyngodon idella*). Preferably, the other fish species is Gold fish (*Carassius aurata*) and the process is repeated a number of times until a substantially attenuated live virus is obtained.

The method may further comprise the step of purifying said isolated virus.

In one specific example, viruses from the 4th transfer (P4) were considered virulent while viruses from the $20^{th}$ transfer (P20 and further) showed reduced virulence and were considered attenuated. From the $25^{th}$ transfer (P25) onwards the viruses totally lost their ability to cause the disease. Clones of the non-virulent virus were isolated and their non-pathogenic character and vaccination potential was evaluated.

Medium and cell extracts harvested from P4 of the virus in cell culture were used for disease induction by intraperitoneal injection and immersion of juvenile naive carp.

In one preferred embodiment, the method of isolating the live-attenuated virus may further comprise the step of drying, preferably through lyophilization of said medium containing the live-attenuated virus, thereby obtaining a dry live-attenuated virus.

According to another embodiment, the method may further comprise the step of adding to the medium and/or to the dry powder, preservatives and/or reducing agents and/or sugars.

In order to stabilize the attenuated virus and to prevent reversion to wild type phenotype, random mutations may be introduced into the viral genome, e.g. through chemical or physical treatments. The chemical treatment may utilize a variety of different mutagens such as 5-bromodeoxyuridine or 5-azacytidine and the physical treatment may utilize ultra violate irradiation (260 nm, 5-30 sec at a distance of 10 cm from the sample). Cells infected with the virus may be treated with the mutagens to determine the dose response curve of each agent. To maximize the probability of isolating mutants, semi lethal doses should be used and plaques are picked up. Mutated viruses are propagated in CFC or KFC, tested for as vaccines by injection with 10-gr fish and challenged with P4 as described before. The same procedure, mutatis mutandis, may be followed in the case of a physical treatment.

With respect to the methods of isolating said carp virus and of isolating said live-attenuated virus, the present invention further encompasses a carp virus obtained by either of said processes.

The present invention further encompasses the use of the live-attenuated virus for the preparation of a vaccine formulation for immunizing fish against the infection caused by the CV virus described hereinbefore. The formulation comprises as an active ingredient, a live-attenuated virus produced as described before.

The term "vaccine" in the context of the present invention, refers to a substance capable of producing an immune response against the infection caused by the virus of the present invention. Such vaccine may produce immunity prophylactically or therapeutically. Vaccines may contain live or inactivated (or "dead") viruses or combinations thereof.

The term "immunization" or "immune response" in the context of the present invention refers to an immunity which can elicit humoral and/or cell mediated immune responses to viral infection, or interfere with the activity, spread, or growth of the virus. Fish immunized by the vaccine of the present invention may experience limited or no growth and spread of the infectious virus.

In one embodiment of the invention, the formulation further comprises an immune modulator adjuvant, stabilizer, antibiotics, immunostimulants or other substances.

Adjuvants have a depot effect and slowly work to stimulate immunity over a long period of time. In fish, weak antigens could only become effective and provide long-term protection when vaccines incorporate adjuvants. These adjuvants are gleaned from those already used in human and veterinary medicine. The adjuvant may be hydrophilic adjuvants, e.g., aluminum hydroxide or aluminum phosphate, or hydrophobic adjuvants, e.g. mineral oil based adjuvants.

Stabilizers such as lactoses may be added to stabilize the vaccine formulation against a variety of conditions such as temperature variations or a freeze-drying process. Antibiotics such as neomycin and streptomycin may be added to prevent the potential growth of germs. The immunostimulants may enhance protection afforded by vaccines and provide non-specific protection against a number of diseases. Many chemicals and other substances have been reported as having immunostimulating properties in fish, i.e., chemicals and glucans, extracts from algae-algines (alginic acid silylic esters) and cytokines.

The live-attenuated virus when used in its dry form in a vaccine may further include a reconstitution fluid, preferably sterile water, saline or physiological solution. It may also contain small amounts of residual materials from the manufacturing process such as cell or bacterial proteins, egg proteins, DNA, RNA, etc. While these materials are not additives per se, they may nonetheless be present in the vaccine formulation.

In another aspect, the present invention provides a vaccine formulation for the immunization of fish against the CV virus, said vaccine formulation comprising the live-attenuated virus as characterized hereinbefore. In one preferred embodiment, the said vaccine formulation further comprises immune modulator adjuvant, stabilizer, antibiotics, immunostimulants or other substances, as described hereinabove.

In one specific embodiment, the formulation comprises said live-attenuated virus in the dry form. In another embodiment, the formulation comprises a tissue culture fluid or fish saline containing said live-attenuated virus, said fluid is preferably maintained at −70° C., most preferably the fluid contains glycerol.

In yet another embodiment, the formulation comprises minced infected fish, or minced fish organs, preferably in the dry form. Said minced infected fish or fish organs may be prepared by the process comprising infecting fish with the attenuated virus and mincing said infected fish, or any organ thereof, 5-6 days post infection.

In one embodiment, said process further comprises drying said minced fish or fish organs, preferably through lyophilization. In another embodiment, the process comprises adding to the minced fish or fish organs and/or to the dry powder preservatives and/or reducing agents and/or sugars.

In one preferred embodiment, the vaccine formulation is prepared by dissolving or suspending the dry live-attenuated virus in at least one reconstitution fluid with no added adjuvant or immunostimulants.

The invention further relates to a method for immunizing fish against the viral infection caused by the CV virus described hereinbefore, said method comprising administration to susceptible fish a vaccine formulation comprised of a live-attenuated CV virus, as described hereinbefore the vaccine being administered in an amount sufficient to induce immunity to subsequent infection by the CV virus.

The live-attenuated virus may be administered to the aquaculture fish individually—orally, e.g. through their feed or by forced oral administration, or by injection. Alternatively the live-attenuated virus may be administered simultaneously to the entire fish population contained in a body of water by spraying, dissolving and/or immersing the virus into said body of water. These methods are useful for vaccination of all kinds of fish, e.g., food and ornamental, and in various environments such as, and not limited to, ponds, aquariums, natural habitat and fresh water reservoirs.

In another aspect, the vaccine is administered to one-day old larvae, to fry approximately at the time of their first ingestion of food or to adult fish.

The invention further provides a vaccine preparation for passive immunization of fish against an infection caused by said CV virus, the vaccine preparation comprising the serum of immunized fish, said serum obtained from animals, i.e., fish, horses, porcine, bovine, mice, rabbits, etc., immunized with the live-attenuated form of said CV virus. In one preferred case, said animals are fish.

The passive immunization may be used as a pre- or post-exposure prophylaxis. It is most useful, however, in ponds and aquaculture where fish have already been exposed to the virus. The vaccine may be administered to the fish by any one or more of the methods disclosed hereinbefore, preferably orally, more preferably by injection.

The invention, with respect to this aspect, further provides a method for treating fish against the infection caused by said CV virus. The method comprises the steps of immunizing an animal with the attenuated CV virus of the present invention, collecting the serum of the immunized animal and treating the fish with said serum, thereby achieving immunization of the fish.

The present invention further provides a genetic construct comprising a nucleotide sequence derived from at least one part of the CV virus. The genetic construct may encompass all naturally occurring genome of the carp virus, cDNA equivalents thereof, and/or all recombinant constructs comprising nucleotide sequences derived from at least one part of the genome of the CV virus.

In a specific embodiment, a vaccine formulation is provided for inducing an immune response in fish, preferably Koi and common carp, comprising an expression vector that includes nucleotide sequences that can induce expression of viral proteins, particularly envelope proteins of the CV virus of the invention. The expression vector may be administered alone or in combination with at least one other nucleotide sequence in the same or in another expression vector, for the simultaneous immunization against at least one additional disease. The expression of the proteins in target cells in the fish will induce the immune response. Where the expression vector encodes proteins or polypeptides associated with a different disease, the resulting immune response may provide immunity both against the CV virus of the invention and the other disease.

By another aspect of the present invention, there is provided a vector that includes nucleotide sequences that can induce expression of viral proteins, particularly envelope proteins of the CV virus of the invention.

One of the uses of said vector is in inducing immune response in an aquacultured fish comprising administering to the fish a vaccine formulation for inducing an immune response, said formulation comprising an expression vector having a nucleotide sequence that encodes for one or more proteins of said carp virus and a control sequence for expression of said nucleotide sequence in carp cells.

The invention further relates to a kit comprising the live-attenuated virus for the treatment of carp virus in fish and instructions on how to use it. The live attenuated-virus may be in its dry form or reconstituted in solution, in the form of a tissue culture fluid maintained at the ambience, preferably at −70° C., or as a solution containing glycerol. The kit may also comprise the live-attenuated virus in the form of a minced fish or fish organs, preferably in its dry form. In case the virus is in its dry form, the kit may further contain a reconstitution fluid. In one preferred embodiment, the live-attenuated virus is dry. In another embodiment, the live-attenuated virus is maintained at −70° C.

The kit may be stored under ambience atmosphere, preferably under vacuum.

The invention further provides an antibody that binds selectively or specifically to the CV DNA virus of the present invention or to a fragment thereof. The term "antibody" refers to IgG, IgM, IgD, IgA, and IgG antibodies. The definition includes polyclonal antibodies or monoclonal antibodies. This term refers also to whole antibodies or fragments of the antibodies comprising the antigen-binding domain of the anti-CLH product antibodies, e.g. antibodies without the Fc portion, single chain antibodies, fragments consisting of essentially only the variable, antigen-binding domain of the antibody, etc. The term "selectively" in the context of the present application, refers to antibodies as defined above which bind with a higher affinity to the CV DNA virus as compared to other DNA viruses and as may be considered significant according to statistical tests.

The invention further relates to a diagnostic kit comprising at least one antibody or at least one conjugated antibody for the diagnosis of the disease associated with the CV virus and instructions how to use it. The kit may further contain at least one control an antigen or a control tissue sample containing said control antigen. The at least one antibody or said at least one conjugated antibody may be in solution or dry. In case the at least one antibody or at least one conjugated antibody is in dry form, the kit may further contain appropriate solutions for the reactions. In one embodiment of the present invention, the at least one conjugate is an enzyme, in which case, the kit may further contain at least one substrate necessary for the detection reaction.

The diagnostic kit of the present application may be used for diagnosing live or dead fish for the presence of the virus of the invention. In accordance with one embodiment, the diagnostic kit may be used to evaluate the degree of immunization of fish post treatment with the vaccine of the present application or with any other vaccine known to a person skilled in the art. In this case, blood may be drawn from live fish and the diagnostic kit may be used to evaluate the extent of immunization, i.e., whether or not the tested fish are sick, and to estimate the extent of infestation. In case it is realized that the fish are not infected, they may then be returned to the aquaculture.

EXAMPLES

General

Fish: Koi or Common carp with an average weight of 42 grams were grown in 500 L tanks with water temperature kept at 22-24° C., receiving fresh water at 0.9 L/min.

Electron Microscopy: Purified virus preparations were negatively stained with 2% phosphotungstate. Grids were examined with Philips 120 electron microscope at 80 kV.

Example 1

Preparation of Cell Cultures

Caudal fins of 50 gr Koi or common carp were removed from anesthetized fish, bathed in 1% sodium hypochloride solutions for 1 min, and then rinsed in 70% ethanol for a few seconds. Fins were then washed three times for 0.5 min in PBS containing penicillin and streptomycin. The fins were transferred to Petri dishes, extensively minced with scissors, and semi-dry small tissue pieces of approximately 1 mm$^3$ placed in dry 50 ml culture flasks. After 60-minute incubation at room temperature, the clumps adhering to the flasks were covered with culture media containing 60% Dulbeco modified Essential medium (DMEM) and 20% Leibovitz L-15 medium (supplied by Biological Industries, Kibbutz Beit Haemek, Israel), 10% fetal calf serum (FCS) (Biological Industries, Kibbutz Beit Haemek, Israel), 10% tryptose phosphate, supplemented with 1% HEPES and antibiotics. During incubation of 10-14 days at 22° C., cells grew out from the tissue to form a monolayer around each clump. The monolayer cultures were trypsinized and transferred into new flasks with fresh medium. The fin clumps may be transferred to new flasks to form a new monolayer culture of primary cells.

Example 2

Purification of the Virus from Culture Medium

Medium harvested from infected CFC was cleared of cells and cell debris by centrifugation for 10 min at 10,000×g. The virus was then pelleted by centrifugation in the Beckman Ti-60 rotor for 50 min at 100,00×g. Pellets were suspended in PBS and loaded on a 15-65% (w/v) sucrose gradient prepared in PBS and centrifuged for 60 min at 110,000×g in the Beckman SW28 rotor. Bands were aspirated from tubes, diluted tenfold in PBS and re-pelleted. Pellets were suspended in PBS and frozen at −75° C. for further investigation.

Example 3

Viral DNA Purification and Plasmid Construction

Purified viral pellets were suspended in TNE buffer (10 mM Tris pH7.8, 100 nM NaCl and 1 nM EDTA) containing 0.5% sodium dodecyl sulphate (SDS). The virus preparation was treated with proteinase K (50 μg/ml) for 3 h. Viral DNA was extracted with phenol, precipitated by ethanol and DNA pellets were suspended in TNE.

Viral DNA was cleaved with BarmHI and EcoRI and fragments were cloned into Bluescript II KS plasmid (Alting et al., Nucl. Acids Res., Vol. 17, 9494, 1989). The inserted viral DNA fragments were sequenced by PCR using T7 and T3 primers and their sequences analyzed by the standard BLAST Program (Altschul et al., Nucl. Acids Res., Vol. 25, 3389-3402, 1997 and Short et al., Nucl. Acids Res., Vol. 16, 7583-7600, 1988).

Example 4

Diagnosis of the Disease by PCR Analysis

Cellular DNA preparations were extracted from cells by phenol and precipitated by ethanol, as described above in Example 3. DNA pellets were suspended in TE (Tris-EDTA) buffer at pH7.4 as described in Sambrook and Russell, Molecular Cloning: A Laboratory Manual, Cold Spring Harbor Laboratory Press, New York, 2001, pp 6.7-6.10). Primers AP1, AP2 and AP3, namely:

5'-CCCATGAGGCTGAGGAACGCCG-3', 5'-GCAC-CCCCGTGATGGTCTTGC-3', and 5'-GGAAGAT-GAGGGCCAGTATGTG-3', respectively, derived from clone D of the viral DNA (see FIG. 6), were used for amplification of viral DNA fragments by PCR. DNA was amplified by 30 cycles at 94° C. for 45 s, 55° C. for 30 s, and 72° C. for 45 s. PCR products were resolved on 1% agarose gel (w/v) and 0.5×TAE and were analyzed.

Example 5

Diagnosis of the Disease by Indirect Immunofluorescence Microscopy

To generate antibodies against the carp virus (CV), a rabbit was immunized with 0.1 mg of purified CV emulsified 1:1 in Freund's complete adjuvant. The rabbit was boosted three times at 10-day intervals with 0.05 mg of purified CV mixed 1:1 in Freund's incomplete adjuvant, and bled three times during 7 to 10 weeks after the first immunization. The serum containing the antibodies was separated from the blood clot and was absorbed on a dry powder prepared from normal fish tissues, to exclude non-specific and non-viral cellular antibodies.

Kidney, spleen, liver and brain were removed from normal and sick fish and were used for the preparation of touch imprint slides. The touch imprint slides were fixed in 3% paraformaldehyde, washed with PBS and blocked by incubation for 60 min with low fat milk containing 50% FCS. The slides were then incubated for 1 h with rabbit anti-CV antibodies, washed with PBS, incubated for 1 h with fluorescein isothiocynate-conjugate swine anti rabbit antibodies, washed with PBS and analyzed with a Nikon Microphot-FX microscope equipped with a 40× planapochromat objective under ultraviolet light.

Use of rabbit CV antiserum determined the localization of the virus in infected fish. Touch imprints of kidney taken from infected fish, but not from naive fish, were positively labeled with the rabbit CV antiserum, indicating that the virus is abundant in the kidneys. These results are in agreement with the PCR experiments and with other experiments showing that the kidney harbors a large amount of the infectious virus. The amount of virus in brain and liver of sick fish was significant but lower than in the kidney as revealed by this technique. The control touch imprint slides of equivalent organs prepared either from naive or sick fish treated with non-inmmunized rabbit serum showed no staining with fluorescent conjugated swine anti-rabbit serum. No viral antigen could be detected in spleen touch imprints or in blood smears derived from sick fish.

Example 6

Diagnosis of the Disease by Testing of Anti Viral Fish Sera

ELISA plates were coated with purified viral preparation and blocked with milk and/or gelatin. Following three washes with PBS the wells were covered with the tested fish sera and incubated at room temperature for 1 hour. The plates were washed again, treated with rabbit anti fish IgB for an hour and washed again. The titer of the fish anti virus sera was determined by using alkaline phosphatase conjugated goat anti rabbit sera, incubated with ELISA substrate and read by an ELISA reader.

Example 7

Diagnosis of the Disease in Fish Droppings

Fish droppings were collected in a tube from the bottom of the tanks (sediment). The water was discarded from the tubes and samples were suspended in PBS at a ratio of 1:5 to 1:10 w/w. Alternatively, naive and sick fingerlings were anesthetized and their hind intestine and intestinal secretions were transferred into 0.5 ml PBS in separate tubes. The intestine samples were washed extensively in PBS and stored at −70° C. until they were used for DNA extraction. The intestine secretions and droppings samples were vortexed vigorously for 2 minutes and centrifuged at 10,000×g for 3 minutes. Supernatants were stored at −70° C. until used for injection, ELISA or PCR tests. For tissue culture experiments samples were also passed through a 0.45 μm Millipore filter.

ELISA and PCR tests were performed as disclosed hereinabove. Results show that viral DNA was identified in the intestine as early as 4 days post infection. In the intestine secretions, viral DNA was identified on day 5 after infection.

The overall findings clearly show that the CV virus is secreted from infected fish via feces and the virus defused from stools into water is infectious and effectively induces the disease.

Example 8

Determining Optimal Fish Age for Immunization

A group of 200 day-old larvae were infected with P4 by immersion for 50 min in a 5 L pool in which 10 ml of P4 solution was added. For twenty days post infection, the larvae were maintained at a water temperature of 23° C. allowing development of the disease. The larvae, which were infected, showed lower survival as compared with the uninfected. Larvae, which survived the infection, were maintained until the age of 45 days. At this stage, the fry were re-infected again with the P4 solution in a procedure identical to that described above for the larvae.

In addition to the fry infected as detailed, a second group of 45-day old fish, of the same hatchery, which previously had not been infected with the virus, were now exposed to the virus for the first time. The fry which survived the infection at the age of one day, showed substantial resistance to the disease at the age of 45 days as compared with the same age fish which were exposed to the virus for the first time.

These experiments showed that 45-day-old fish (of 7 gr) and older are immunized very well. Fish of smaller weight, namely 2.5-3 gr, are immunized as well but a higher mortality of about 20% is observed.

Example 9

Infection of Fish with the Virulent Virus

Several groups each containing 50 10-gr fish were infected with the P4 pathogenic virus by injecting each fish with 0.2 ml of the virus (I.P). The control groups consisted of fish that were injected with physiological solutions (PBS). As FIG. 7A shows, 80% of the fish died 10-25 days post-injection.

Fish which survived the infection, i.e., 20 fish of the infected group and 50 of the control group were re-infected after a period of 35 days. The re-infection was achieved by cohabitation with diseased fish. As FIG. 7B shows, fish that survived the initial infection were immune to the virus, with only 30% of the fish dying of the disease. However, high mortality of nearly 100% was observed in fish, which were exposed to the virus for the first time.

Example 10a

Infection of Fish with Live Attenuated Virus

Two groups of fish each containing 25 10-gr. fish, were injected (I.P) with 0.3 ml of the P25 attenuated virus, with a concentration of $6 \times 10^3$ PFU/ml. As a negative control group, 25 fish were injected with saline and as a positive control group, 25 fish were injected with the virulent P4 virus at a concentration of $0.3 \times 10^3$ PFU/ml. Upon injection, the fish were kept under conditions allowing development of the disease for 30 days.

As may be observed from FIG. 8A, nearly all fish injected with the attenuated virus did not develop the disease, as compared with those injected with the virulent form.

Fish which were injected with the attenuated virus and survived were challenged by re-exposure to the virus, 30 days after the initial exposure, by cohabitation with diseased fish. As FIG. 8B shows, the fish exhibited a high degree of resistance to the disease. Only about 5% of the fish initially exposed to the attenuated virus by injection were infected.

This experiment demonstrates the ability of the attenuated live virus to immunize the fish against the carp virus. This type of experiment was repeated 3 times, with similar results.

Example 10b

Effectiveness of the Attenuated Virus

Koi Fin Cells (KFC) were infected with diluted CV virus of transfer P26 and then overlaid with agar. Viruses from four separate plaques were harvested, tittered and injected intra-peritonealy into naive fish. A control group of fish was injected with PBS. The mortality of the fish was monitored for 25 days, during which time very few fish died. On day 25, the fish were challenged by cohabitation with sick fish to assess their resistance to the disease. As may be concluded from FIG. 9, 95% of the uninfected control group died shortly after cohabitation. None of the fish injected with the cloned viruses showed symptoms of the disease and no mortality was observed. These results clearly indicate that the clones derived from transfer P26 confer immunity against the infection induced by CV virus.

Example 11

Preparation of the Dry Live-Attenuated Virus

The virus isolated as detailed in Example 1 was passaged at least 30 times in a series of carp cell lines, and then transferred under restricted conditions and under high dilutions. Plaques obtained were observed to be morphologically different from those produced by the virulent virus. Viruses from the $4^{th}$ transfer, P4, were determined virulent. From the $20^{th}$ transfer onwards (P20), the ability of the virus to cause disease was attenuated. Viruses from the $25^{th}$ transfer (P25) onwards and their clones and subdlones totally lost their ability to cause the disease.

Culture medium from infected cell cultures of transfer P20 were harvested and divided into two different tubes. One of the two tubes was stored at $-70°$ C. The second tube was frozen and lyophilized, after which time a yellow powder was obtained and incubated at room temperature for two hours. No preservatives such as reducing agents or sugars were added. The dry virus may be maintained at the ambience, preferably in vials under vacuum.

In order to determine the virulence of the freeze-dried virus, a sample of dry virus was reconstituted and tittered on fresh CFC. In parallel, a frozen sample obtained from the first tube was thawed and used to infect fresh cultures, as a control. The number of plaques was counted and it was determined that the titer of the dry virus was 5-10 times lower as compared with the control.

The reconstitution of the dry virus was achieved with purified, sterile water.

Example 12

Kinetics of Anti-CV Antibody Formation Following Immunization with Attenuated Virus A group of five fish was injected with the attenuated virus at day 0. The fish were then bled on marked days post injection and the level of the anti CV antibodies in the sera was evaluated by the following procedure. Wells of ELISA plates were covered with the CV virus and were blocked with milk prior to the addition of fish sera. To be accurate the fish sera was diluted to the following dilution ratios: 1:100, 1:500, 1:2,500, and 1:12,500. Following intensive washings of each of the wells, they were covered with rabbit anti fish Fc, as previously described, for 60 minutes at room temperature. Further treatment with AP conjugated goat anti rabbit IgG followed.

As FIG. 10 clearly shows, the fish sera contains high levels of anti CV antibodies. The antibodies appear between 7-14 days post infection. Their titer increases and reaches a high level on day 21, at which level it remains for at least 51 days post infection. This study clearly shows that the attenuated virus induces a high level of anti CV antibodies.

Example 13

Preparation of Vaccine for Passive Immunization

A group of 15 fish were injected three times with the attenuated virus of the present invention, at a concentration of 200-2000PFU/Inj at 15 day intervals. 15-20 days after last inoculation the fish were bled, the anti-CNGV serum was isolated by one of the methods known to a person skilled in the art, and stored at $-70°$ C. Alternatively, the serum samples were lyophilized and kept until used.

A group of 50 fish were exposed during a period of 2-4 days to the CV virus by cohabitation with sick fish. Each of the 50 fish was then injected with the anti-CNGV serum and the development of the disease was monitored.

It was found that fish injected with the anti-CNGV serum did not develop the disease, while non-immunized fish developed the disease and died within 18 days from the cohabitation with the disease species.

Example 14

Preparation of an Inactivated Virus

The virulent virus was placed at a distance of 10 cm away from a UV lamp and irradiated at 260 nm for about 2 minutes. At the end of the 2-minute period, irradiation was terminated and the virus was then administered to the fish as described in the previous examples.

After the irradiation is terminated, the virus is tested for the development of plaques, as described before. Samples which do not develop plaques are considered inactivated and used for immunization of the fish.

Repeated experiments showed that irradiation of the virulent virus samples to periods of only several seconds yielded activated virus which underwent random mutation.

Example 15

Immunizing Fish with a Combination Treatment of Inactivated Virus Followed by the Live-attenuated Virus A group of 32 healthy fish were injected with the inactivated virus. After 5 days the fish were injected by the live-attenuated virus in accordance with the procedure detailed hereinbefore. The fish were exposed by cohabitation to diseased fish for a period of 10 days. None of the immunized fish exhibited behavior characteristic with the infectious disease (results not shown).

Example 16

Whole DNA Vaccine

The total DNA of the CV viral genome was extracted from the purified virus, which was isolated as described hereinbefore, precipitated by ethanol, dissolved in water and used for the treatment of the fish (*Cyprinus carpio*). Three different dosages were prepared and injected to the fish muscles: (1) 10 ng of the DNA per fish; (2) 100 ng DNA per fish; and (3) 1 ug DNA per fish. DNA preparations were introduced to the fish muscles by 4-6 injections. Twenty 10gr fish were used in each group. After 20 days, each of the treated fish groups were challenged with the virulent virus and the survivors were counted daily.

Fish administered with 10 ng of the DNA per fish showed 15% vitality; 20% vitality was observed in fish groups (n=50) administered with 100 ng DNA per fish; and 55% vitality was observed in groups (n=50) of fish administered with 1 µg DNA per fish (Control—20% vitality).

Example 17

Cloning into a pCDNA3 Vector

The following genes were introduced into plasmids:

1. Major capsid protein, GenBank Accession No. AAY41899
2. Glycoprotein, GenBank Accession No. AAY67836
3. Membrane protein (ORF 2), GenBank Accession No. BAD18064
4. Major envelope protein (ORF4), GenBank Accession No. BAD18066
5. Membrane protein (ORF3), GenBank Accession No. BAD18065

The above fragments 1 and 2 were obtained according to the following procedure: Purified viral proteins were first separated on PAGE. Fish anti-sera, isolated from fish which were preimmunized with the virus, were used to define the viral immunogenic proteins. These proteins were extracted from the gels, digested by trypsin, and the amino acid sequences of several peptides were determined by using Mass Spectroscopy, according to procedures known to a person skilled in the art. Based on the amino acid sequences of the peptides, the generative oligonucleotides were synthesized and were used as primers to amplify the appropriate gene fragments on the viral DNA as template. The amplified fragments were cloned, sequenced and by gene walking method the sequence of the entire genes were obtained. The complete genes were then cloned into a pCDNA3 plasmid.

Example 17B

Cloning the Entire Viral Genome as a Bacterial Artificial Chromosome (BAC) in *E. coli*

This procedure followed similar procedures described in: Meseda et al., Virology, 318: 420-428 (2004) and in Brune et al., TIG, 16: 254-259 (2000).

Generally, the BAC fragment (~8000bp) was introduced into the center (550 and 670 bp) of the ribonucleotide reductase gene fragment (RNR). The DNA fragments containing the RNR with the BAC sequences were inserted into BlueScript plasmid and propagated in bacterial cells. The DNA was used for transfection of CV infected cells (KFC). This fragment, containing the BAC was integrated into the entire viral genome by homologous recombination in the fish cells. The recombinant viruses were selected, their genomic DNA preparations were extracted and the circular genome intermediates were then isolated from infected cells. The circular BAC-CV DNA was used for electroporation of the DNA into *E. coli*, in order to achieve high amounts of the BAC-CV DNA.

The BAC-CV construct which efficiently multiplied in the bacterial cells was used to introduce mutations, deletions or insertions. The methodology for such genetically a modification is known to a person skilled in the art.

The BAC mutated DNA can now be used for DNA immunization, or for transfection of KFC in order to harvest mutated viruses.

The invention claimed is:

1. An isolated avirulent form of a CV DNA virus that causes viral disease in fish, the CV DNA virus being a double stranded DNA virus having a capsid with a icosahedron morphology, the capsid being of about 90-110 nm in size as determined by electron microscopy, the DNA of the CV DNA virus having between about 250,000 and 300,000 base pairs.

2. An isolated avirulent form of a CV DNA virus that causes viral disease in fish, the CV DNA virus being a double stranded DNA virus having a capsid with a icosahedron morphology, the capsid being of about 90-110 nm in size as determined by electron microscopy, the DNA of the CV DNA virus having between about 260,000 and 285,000 base pairs.

3. An isolated avirulent form of a CV DNA virus that causes viral disease in fish, the CV DNA virus being a double stranded DNA virus having a capsid with a icosahedron morphology, the capsid being of about 90-110 nm in size as determined by electron microscopy, the DNA of the CV DNA virus having about 277,000 base pairs.

4. The isolated avirulent form of the CV DNA virus of claim 1 being a live-attenuated virus or an inactivated virus form of the CV DNA virus.

5. The isolated avirulent form of the CV DNA virus of claim 1, wherein the fish are of the *Cyprinus carpio* species.

6. The isolated avirulent form of the CV DNA virus of claim 4, being a live-attenuated CV DNA virus, being deposited at the Collection Nationale de Cultures De Microorganismes (CNCM), Institut Pasteur, Paris, under accession no. CNCM I-3146.

7. An isolated avirulent form of the CV DNA virus of claim 4, being a live-attenuated CV DNA virus having the ability of inducing an anti-carp DNA virus immune response in the fish without the virulence associated with said CV DNA virus.

8. The isolated avirulent form of the CV DNA virus of claim 4, being an inactivated virus form of the CV DNA virus and having the ability of inducing an anti-carp DNA virus immune response in the fish without the virulence associated with the CV DNA virus.

9. A method for the isolation of a live-attenuated carp DNA virus, comprising seeding of a virulent virus which causes viral disease in fish in fish cell culture, said virulent virus being a double stranded DNA virus having a capsid with a icosahedron morphology, the capsid being of about 90-110 nm in size as determined by electron microscopy, the DNA of the virus having between about 250,000 and 300,000 base pairs, identifying plaques caused by a virus with a reduced virulence and isolating the progeny virus from such a plaque.

10. The method of claim 9, wherein the isolated viruses are again seeded on a fish cell culture and the process is repeated a number of times until a substantially attenuated live virus is obtained.

11. An isolated live-attenuated CV DNA virus obtained by the method, comprising:

seeding of a virulent virus which causes viral disease in fish cell culture, said virulent virus being a double stranded DNA virus having a capsid with a icosahedron morphology, the capsid being of about 90-110 nm in size as determined by electron microscopy, the DNA of the virus having between about 250,000 and 300,000 base pairs;

identifying plaques caused by a virus with a reduced virulence; and isolating the progeny virus from such a plaque.

12. The isolated live-attenuated CV DNA virus of claim 11, wherein the isolated viruses are again seeded on a fish cell culture and the process is repeated a number of times until a substantially attenuated live CV DNA virus is obtained.

13. An immunogenic formulation for immunizing fish against an infection caused by a CV DNA virus which causes viral disease in fish, the CV DNA virus being a double stranded DNA virus having a capsid with a icosahedron morphology, the capsid being of about 90-110 nm in size as determined by electron microscopy, the DNA of the CV DNA virus having between about 250,000 and 300,000 base pairs, the immunogenic formulation comprising an avirulent form of the CV DNA virus of claim 1.

14. The immunogenic formulation of claim 13, wherein the avirulent form is a live-attenuated CV DNA virus having the ability of inducing an anti-carp DNA virus immune response in the fish without the virulence associated with the CV DNA virus.

15. A method for immunizing fish against viral infection which causes viral disease in fish, said infection is caused by a DNA virus having a double stranded DNA having a capsid with a icosahedron morphology, the capsid being of about 90-110 nm in size as determined by electron microscopy, the DNA of the virus having between about 250,000 and 300,000 base pairs, comprising administering to susceptible fish an immunogenic formulation composed of a live-attenuated virus form of claim 1 in an amount sufficient to induce immunity to subsequent infection by the carp virus.

16. The method according to claim 15, wherein the immunogenic formulation is administered to the aquaculture.

17. The method of claim 15, wherein the step of administering the immunogenic formulation comprises injection to individual fish, or spray or immersion of the formulation into the aquaculture.

18. The method of claim 15, wherein the immunogenic formulation is administered to the fish orally via food.

19. A kit comprising the isolated live-attenuated form of the CV DNA virus of claim 1 for the treatment against carp virus in fish and instructions on how to use it.

20. An immunogenic formulation for immunizing fish against an infection caused by a CV DNA virus which causes viral disease in fish, the CV DNA virus being a double stranded DNA virus having a capsid with a icosahedron morphology, the capsid being of about 90-110 nm in size as determined by electron microscopy, the DNA of the CV DNA virus having between about 250,000 and 300,000 base pairs, said immunogenic formulation comprising the serum of animals immunized with the live-attenuated form of the CV DNA virus of claim 1.

* * * * *

SEQUENCE LISTING

```
<160> NUMBER OF SEQ ID NOS: 3

<210> SEQ ID NO 1
<211> LENGTH: 22
<212> TYPE: DNA
<213> ORGANISM: FISH VIRAL DNA

<400> SEQUENCE: 1
cccatgaggc tgaggaacgc cg                                            22

<210> SEQ ID NO 2
<211> LENGTH: 21
<212> TYPE: DNA
<213> ORGANISM: FISH VIRAL DNA

<400> SEQUENCE: 2 gcaccccgt gatggtcttg c                                              21

<210> SEQ ID NO 3
<211> LENGTH: 22
<212> TYPE: DNA
<213> ORGANISM: FISH VIRAL DNA

<400> SEQUENCE: 3
ggaagatgag ggccagtatg tg                                            22
```